United States Patent [19]

Shioya et al.

[11] Patent Number: 5,144,054

[45] Date of Patent: Sep. 1, 1992

[54] SILOXANE DERIVATIVES, PRODUCING METHOD THEREOF AND AGENTS INCLUDING SILOXANE DERIVATIVE

[75] Inventors: Yasushi Shioya, Chiba; Yuji Suzuki, Sakura; Ken Takeuchi, Haga; Koji Yoshino; Akira Kawamata, both of Utsunomiya, all of Japan

[73] Assignee: Kao Corporation, Tokyo, Japan

[21] Appl. No.: 750,535

[22] Filed: Aug. 27, 1991

[30] Foreign Application Priority Data

Aug. 30, 1990 [JP] Japan .................................. 2-228958
Sep. 26, 1990 [JP] Japan .................................. 2-256732

[51] Int. Cl.$^5$ .......................... C07F 7/08; C08G 77/04
[52] U.S. Cl. .................................... 556/445; 556/449; 556/450; 556/453; 556/469
[58] Field of Search .............. 556/445, 449, 450, 453, 556/466, 467, 25, 29

[56] References Cited

U.S. PATENT DOCUMENTS

| | | | |
|---|---|---|---|
| 5,001,248 | 3/1991 | Grabowski | 556/445 X |
| 5,032,662 | 7/1991 | Berger et al. | 556/445 X |
| 5,059,704 | 10/1991 | Petroff et al. | 556/445 X |

*Primary Examiner*—Arthur C. Prescott
*Attorney, Agent, or Firm*—Oblon, Spivak, McClelland, Maier & Neustadt

[57] ABSTRACT

Novel siloxane derivatives represented by general formula (1):

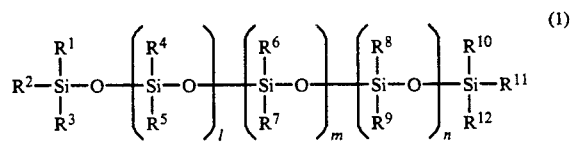

A method for producing the siloxane derivatives and agents such as cosmetic preparations, emulsifying dermatotherapeutic external agents and the like including at least one of the siloxane derivatives are also disclosed.

14 Claims, No Drawings

SILOXANE DERIVATIVES, PRODUCING METHOD THEREOF AND AGENTS INCLUDING SILOXANE DERIVATIVE

BACKGROUND OF THE INVENTION i) Field of the Invention

The present invention relates to novel siloxane derivatives having surface active action useful as an emulsifier, a method for producing the novel siloxane derivatives, and agents including a novel siloxane derivative such as cosmetic preparations, emulsifying dermatotherapeutic external agents making use thereof and the like.

ii) Description of the Background Art

Conventionally, silicone compounds having surface active action are divided into four groups such as compounds having an anionic hydrophilic group, compounds having a cationic hydrophilic group, compounds having a betaine hydrophilic group and compounds having a nonionic hydrophilic group according to kinds of denatured hydrophilic groups.

As to the compounds having a nonionic hydrophilic group, polyoxyalkylene denatured silicone surfactants having a polyoxyalkylene group as a hydrophilic group are known. However, these are inferior in emulsifying stability, and, when it is used as an emulsifier such as cosmetic preparations or the like, in order to obtain sufficient emulsifying stability, a thickener or thickeners such as silica, clay mineral and the like must be further added to.

On the other hand, a polyalcoholic hydroxyl group as the nonionic hydrophilic group excepting the polyoxyalkylene group can be thought of, but now silicone surfactants having a plyalcoholic hydroxyl group as a hydrophilic group are hardly known except that a polyglycerin denatured silicone disclosed in Japanese patent publication No. Sho 62-34039 and a sorbitan denatured silicone disclosed in Japanese patent laid-open No. Sho 57-209295 are known so as to exhibit the surface active action.

Further, silicone compounds denatured by a glyceryl group as a polyalcoholic hydroxyl group are known, as disclosed in Japanese patent laid-open Nos. Sho 62-195389, 64-16793 and 63-101388, but these compounds are surface modifiers making use of reactivity of the hydroxyl group for synthetic resins, and their surface active actions are unknown.

As described above, there is practically nothing at all of nonionic silicone surfactant having sufficient capability up to now.

In the meantime, conventionally, water-in-oil type emulsifying dermatotherapeutic external agents represented by water-in-oil type emulsifying cosmetic preparations have been widely used in virtue of their excellent properties such as good fitness to a skin due to a film formed on a skin surface, good cosmetic adhesiveness and the like.

However, on the contrary, the water-in-oil type emulsifying dermatotherapeutic external agents have drawbacks such as bad slip on applying, strong oiliness and stickiness feelings and the like. Hence, recently, silicone oils as an oil solution having less sticky or plain and smooth usage feelings and excellent water repellency have been mostly used, but it is difficult to emulsify the silicone oils and thus extremely difficult to obtain an emulsifying system having excellent stability.

Therefore, it has been desired to develop novel emulsifiers capable of stably emulsifying not only usual oil solutions but also silicone oils and giving good usage feeling when applying on a skin.

SUMMARY OF THE INVENTION

Accordingly, it is an object of the present invention to provide novel siloxane derivatives having surface active action useful as an emulsifier capable of realizing excellent emulsification stability and having good fitness, good slip, good cosmetic adhesiveness, good usage feeling.

It is another object of the present invention to provide a method for producing novel siloxane derivatives having surface active action useful as an emulsifier capable of realizing excellent emulsification stability and having good fitness, good slip, good cosmetic adhesiveness, good usage feeling.

It is further object of the present invention to provide agents such as cosmetic preparations and emulsifying dermatotherapeutic external agents including a novel siloxane derivative having surface active action useful as an emulsifier capable of realizing excellent emulsification stability and having good fitness, good slip, good cosmetic adhesiveness, good usage feeling.

In accordance with one aspect of the present invention, there is provided a siloxane derivative represented by general formula (1)

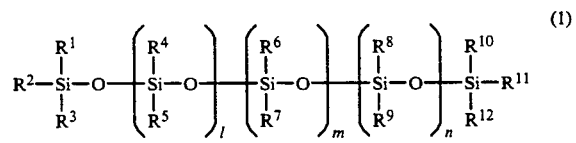

wherein at least one of $R^1$ to $R^{12}$ is a group represented by general formula (2)

wherein Q is a divalent hydrocarbon group having 3 to 20 carbon atoms, $R^{13}$ and $R^{14}$ are hydrogen atom or a hydrocarbon group having 1 to 5 carbon atoms, and at least one of $R^{13}$ and $R^{14}$ is hydrogen atom; the remainings of $R^1$ to $R^{12}$ are straight-chain, branched-chain or cyclic hydrocarbon groups having 1 to 30 carbon atoms or groups represented by general formula (3)

wherein X is a divalent hydrocarbon group having an ether bonding and/or ester bonding and $R^{15}$ is a straight-chain, branched-chain or cyclic hydrocarbon group having 1 to 30 carbon atoms; l, m and n are numbers of 0 to 2,000, and at least one of $R^1$ to $R^3$ and $R^{10}$ to $R^{12}$ is a group represented by general formula (2) when $l+m+n=0$ except that one of $R^1$ to $R^{12}$ is a group represented by general formula (2) wherein Q is trimethylene and $R^{13}$ and $R^{14}$ are both hydrogen atoms; and the remainings of $R^1$ to $R^{12}$ are all methyl groups.

In a preferable siloxane derivative, Q is an alkylene group having 3 to 20 carbon atoms and $R^{13}$ and $R^{14}$ are hydrogen atoms, and wherein $R^1$ to $R^{12}$ are alkyl groups having 1 to 30 carbon atoms.

In the siloxane derivative, $l+m+n$ can be 0 to 2,000 and Q can be an alkylene group having 3 to 20 carbon atoms.

Further preferable siloxane derivatives are represented by general formulas (1A) to (1D)

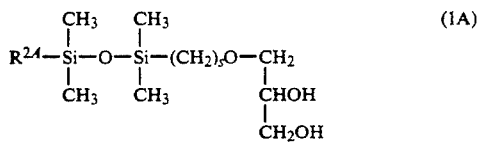

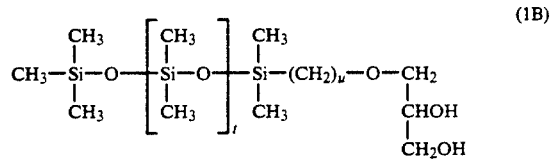

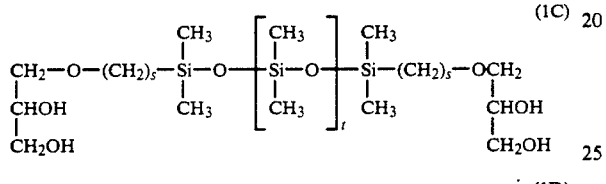

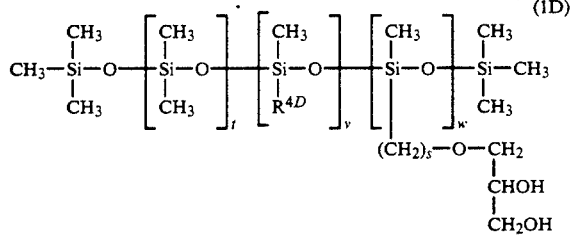

In accordance with another aspect of the present invention, there is provided a method for producing a siloxane derivative represented by general formula (1a)

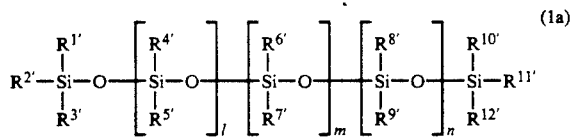

wherein at least one of $R^{1'}$ to $R^{12'}$ represents a group represented by general formula (2), the remainings of $R^{1'}$ to $R^{12'}$ are straight-chain, branched-chain or cyclic hydrocarbon groups having 1 to 30 carbon atoms, and at least one of $R^{1'}$ to $R^{3'}$ and $R^{10'}$ to $R^{12'}$ represents a group represented by general formula (2) when $l+m+n=0$ except that one of $R^{1'}$ to $R^{12'}$ represents a group represented by general formula (2) wherein Q represents trimethylene and $R^{13}$ and $R^{14}$ represent both hydrogen atoms, and the remainings of $R^1$ to $R^{12}$ represent all methyl groups, comprising reacting a compound represented by general formula (4)

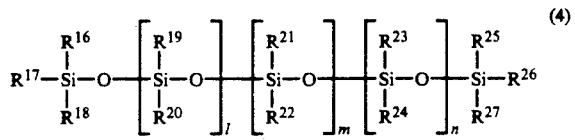

wherein at least one of $R^{16}$ to $R^{27}$ represents hydrogen atom, the remainings of $R^{16}$ to $R^{27}$ represent a straight-chain, branched-chain or cyclic hydrocarbon group having 1 to 30 carbon atoms, l, m and n are numbers of 0 to 2000, and at least one of $R^{16}$ to $R^{18}$ and $R^{25}$ to $R^{27}$ represents hydrogen atom when $l+m+n=0$, with a compound represented by general formula (2')

In formula (2'), Q' represents a hydrocarbon group having 3 to 20 carbon atoms and one double bond, and $R^{13}$ and $R^{14}$ are the same as described above.

In accordance with further aspect of the present invention, there is also provided a method for producing a siloxane derivative represented by general formula (1b)

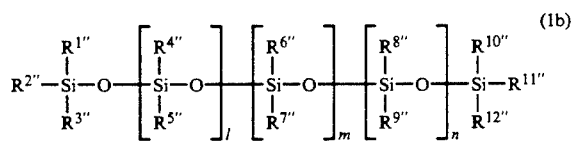

wherein at least one of $R^{1''}$ to $R^{12''}$ represents a group represented by general formula (2), at least one of the remainings of $R^{1''}$ to $R^{12''}$ represents a group represented by general formula (3), and the remainings of $R^{1''}$ to $R^{12''}$ are straight-chain, branched-chain or cyclic hydrocarbon groups having 1 to 30 carbon atoms, and, when $l+m+n=0$, at least one of $R^{1''}$ to $R^{3''}$ and $R^{10''}$ to $R^{12''}$ represents a group represented by general formula (2) and at least one of the remainings of $R^{1''}$ to $R^{3''}$ and $R^{10''}$ to $R^{12''}$ represents a group represented by general formula (3), comprising reacting a compound represented by general formula (4')

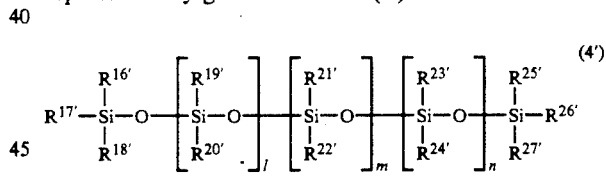

wherein at least two of $R^{16'}$ to $R^{27'}$ represent hydrogen atoms, the remainings of $R^{16'}$ to $R^{27'}$ represent a straight-chain, branched-chain or cyclic hydrocarbon group having 1 to 30 carbon atoms, l, m and n are the same as described above, and at least two of $R^{16'}$ to $R^{18'}$ and $R^{25'}$ to $R^{27'}$ represent hydrogen atoms when $l+m+n=0$, with compounds represented by general formulas (2') and (3')

wherein X' is a hydrocarbon group having at least one double bond and an ether bonding and/or ester bonding and $R^{15}$ is the same as described above.

The siloxane derivative represented by general formula (1) is used as an emulsifier.

A cosmetic preparation includes a siloxane derivative represented by general formula (1).

A emulsifying dermatotherapeutic external agent includes (A) 5 to 70 weight % of oil phase component; (B) 20 to 94.9 weight % of water phase component; and (C) 0.1 to 30 weight % of emulsifier including a siloxane derivative represented by general formula (1).

In a preferable emulsifying dermatotherapeutic external agent, the oil phase component (A) includes at most 50 weight % of silicone oil, and in the siloxane derivative of the component (C), $l+m+n$ is 0 to 2,000, and Q is an alkylene group having 3 to 20 carbon atoms.

In another preferable emulsifying dermatotherapeutic external agent, the oil phase component (A) includes 50 weight % of silicone oil, and the siloxane derivative in the component (C) is represented by either general formula (1A)

DETAILED DESCRIPTION OF THE INVENTION AND PREFERRED EMBODIMENTS

The present invention will now be described in detail with reference to Examples thereof.

Under the actual circumstances, researches have been carried out to find that novel siloxane derivatives having a glyceryl group, as hereinafter described in detail, are suitable nonionic surfactants as emulsifiers of cosmetic preparations, dermatotherapeutic external agents and the like to bring about the completion of the present invention.

That is, according to the present invention, there are provided novel siloxane derivatives represented by general formula (1), a method for producing the siloxane derivatives and agents such as cosmetic preparations, emulsifying dermatotherapeutic external agents and the like including at least one of the siloxane derivatives: In general formula (1), at least one of $R^1$ to $R^{12}$ is a group represented by general formula (2)

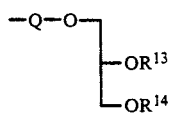
(2)

wherein Q is a divalent hydrocarbon group having 3 to 20 carbon atoms, $R^{13}$ and $R^{14}$ are hydrogen atom or a hydrocarbon group having 1 to 5 carbon atoms, and at least one of $R^{13}$ and $R^{14}$ is hydrogen atom; the remainings of $R^1$ to $R^{12}$ are straight-chain, branched-chain or cyclic hydrocarbon groups having 1 to 30 carbon atoms or groups represented by general formula (3)

$$-X-R^{15} \tag{3}$$

wherein X is a divalent hydrocarbon group having an ether bonding and/or ester bonding and $R^{15}$ is a straight-chain, branched-chain or cyclic hydrocarbon group having 1 to 30 carbon atoms; l, m and n are numbers of 0 to 2,000, and at least one of $R^1$ to $R^3$ and $R^{10}$ to $R^{12}$ is a group represented by general formula (2) when $l+m+n=0$ except that one of $R^1$ to $R^{12}$ is a group represented by general formula (2) wherein Q is trimethylene and $R^{13}$ and $R^{14}$ are both hydrogen atoms; and the remainings of $R^1$ to $R^{12}$ are all methyl groups.

In general formula (2), as to the divalent hydrocarbon group having 3 to 20 carbon atoms, represented by Q, an alkylene group having 3 to 20 hydrogen atoms is preferable, and more specifically, for example, straight-chain alkylene such as trimethylene, tetramethylene, pentamethylene, hexamethylene, heptamethylene, octamethylene, nonamethylene, decamethylene, undecamethylene, dodecamethylene, tetradecamethylene, hexadecamethylene, octadecamethylene or the like, branched-chain methylene such as propylene, 2-methyltrimethylene, 2-methyltetramethylene, 2-methylpnetamethylene, 3-methylpentamethylene or the like are given. Regarding the hydrocarbon group having 1 to 5 carbon atoms, represented by $R^{13}$ and $R^{14}$, straight-chain, branched-chain or cyclic alkyl groups such as methyl group, ethyl group, propyl group, butyl group, pentyl group, isopropyl group, sec-butyl group, t-butyl group, neopentyl group, cyclopentyl group and the like are given.

In general formula (3), as regards the divalent hydrocarbon group having the ether bonding and/or ester bonding, represented by $X,+CH_2)r-(OC_2H_4-)p-(OC_3H_6)q-O-$ wherein r is integer of 3 to 20 and p and q are number of 0 to 50, $-(OCH_2)_r-O-CO-$, $-(OCH_2)_r-COO-$ and the like are given. As to the straight-chain, branched-chain or cyclic hydrocarbon group having 1 to 30 carbon atoms, represented by $R^{15}$, straight-chain alkyl groups such as methyl group, ethyl group, propyl group, butyl group, pentyl group, hexyl group, octyl group, decyl group, dodecyl group, tetradecyl group, hexadecyl group, octadecyl group, eicocyl group, dococyl group, tetracocyl group, hexacocyl group, octacocyl group, triacontyl group and the like; branched-chain alkyl groups such as isopropyl group, sec-butyl group, t-butyl group, neopentyl group, 1-ethylpropyl group, 1-heptyldecyl group and the like; and cyclic alkyl groups such as cyclopentyl group, cyclohexyl group, abietyl group, cholesteryl group and the like are given. As to l, m and n, a range of 0 to 2000 is preferable in view of availability of raw materials of organohydrogen polysiloxanes, operability in manufacturing and the like.

In the siloxane compounds represented by general formula (1), a compound or compounds in which Q in general formula (2) represented by at least one of $R^1$ to $R^{12}$ is an alkylene group having 3 to 30 carbon atoms, $R^{13}$ and $R^{14}$ are both hydrogen atoms, and the remainings of $R^1$ to $R^{12}$ are alkylene groups having 1 to 30 carbon atoms can be preferably in particular.

In the siloxane compounds represented by general formula (1), more preferable compounds are shown by formulas (1A), (1B), (1C) and (1D) as follows.

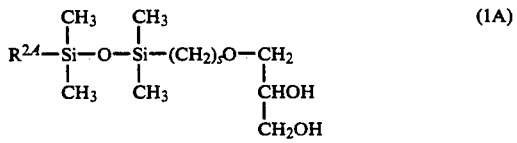
(1A)

In this formula, $R^{24}$ represents an alkyl group having 2 to 30 carbon atoms and s is a number of 3 to 20.

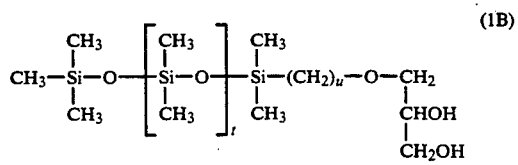
(1B)

In this formula, t is a number of 0 to 2000 and u is a number of 3 to 20.

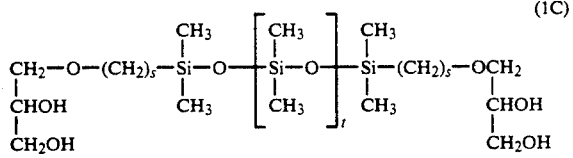

(1C)

In this formula, t is a number of 0 to 2000 and s is a number of 3 to 20.

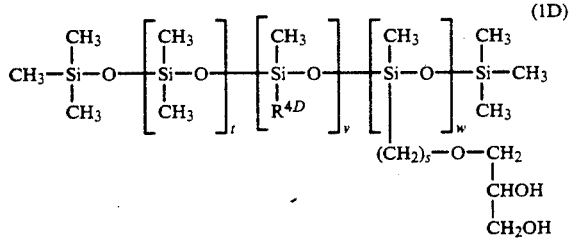

(1D)

In this formula, $R^{4D}$ represents an alkyl group having 2 to 30 carbon atoms, t and v are numbers of 0 to 1000, w is a number of 1 to 1000, and s is a number of 3 to 20.

According to the present invention, the siloxane compounds represented by general formula (1) can be prepared in accordance with reaction schemes as follows.

(i) Preparation of a Siloxane Compound (1a) Having no Group Represented by General Formula (3) from Compounds (4) and (2')

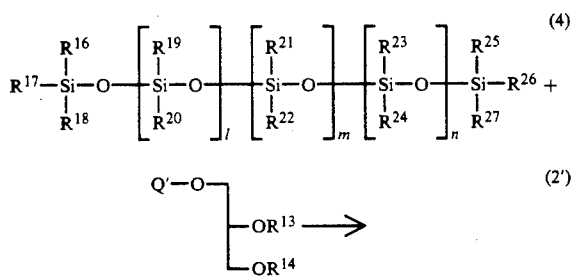

(4)

(2')

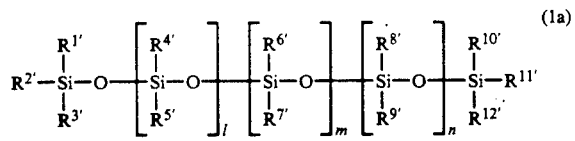

(1a)

In formula (4), at least one of $R^{16}$ to $R^{27}$ represents hydrogen atom, the remainings of $R^{16}$ to $R^{27}$ represent a straight-chain, branched-chain or cyclic hydrocarbon group having 1 to 30 carbon atoms, l, m and n are numbers of 0 to 2000, and at least one of $R^{16}$ to $R^{18}$ and $R^{25}$ to $R^{27}$ represents hydrogen atom when $1+m+n=0$. In formula (2'), Q' represents a hydrocarbon group having 3 to 20 carbon atoms and one double bond, and $R^{13}$ and $R^{14}$ are the same as described above. In formula (1a), at least one of $R^{1'}$ to $R^{12'}$ represents a group represented by general formula (2), the remainings of $R^{1'}$ to $R^{12'}$ are straight-chain, branched-chain or cyclic hydrocarbon groups having 1 to 30 carbon atoms, and at least one of $R^{1'}$ to $R^{3'}$ and $R^{10'}$ to $R^{12'}$ represents a group represented by general formula (2) when $1+m+n=0$ except that one of $R^{1'}$ to $R^{12'}$ represents a group represented by general formula (2) wherein Q represents trimethylene and $R^{13}$ and $R^{14}$ represent both hydrogen atoms, and the remainings of $R^1$ to $R^{12}$ represent all methyl groups.

That is, an organohydrogen polysiloxane (4) having at least one silicon-hydrogen bonding is reacted with an alkenylglyceryl ether (2') to obtain a siloxane derivative (1a) having no group represented by general formula (3). (ii) Preparation of a siloxane compound (1b) having a group represented by general formula (3) from compounds (4'), (2') and (3').

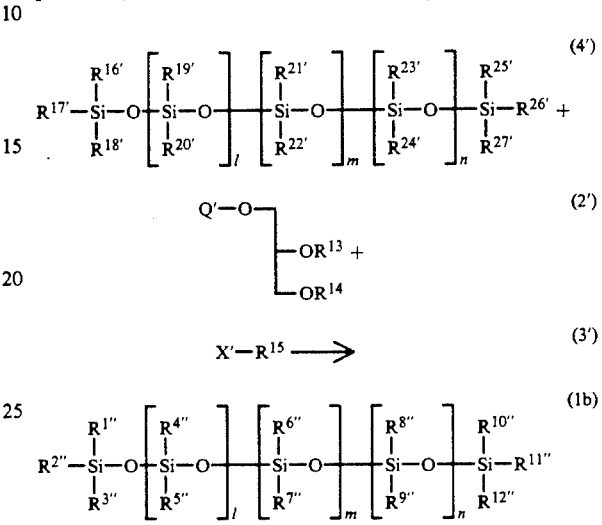

In formula (4'), at least two of $R^{16'}$ to $R^{27'}$ represent hydrogen atoms, the remainings of $R^{16'}$ to $R^{27'}$ represent a straight-chain, branched-chain or cyclic hydrocarbon group having 1 to 30 carbon atoms, l, m and n are the same as described above, and at least two of $R^{16'}$ to $R^{18'}$ and $R^{25'}$ to $R^{27'}$ represent hydrogen atoms when $1+m+n=0$. In formula (2'), Q', $R^{13}$ and $R^{14}$ are the same as described above. In formula (3'), X' is a hydrocarbon group having at least one double bond and an ether bonding and/or ester bonding and $R^{15}$ is the same as described above. In formula (1b), at least one of $R^{1''}$ to $R^{12''}$ represents a group represented by general formula (2), at least one of the remainings of $R^{1''}$ to $R^{12''}$ represents a group represented by general formula (3), and the remainings of $R^{1''}$ to $R^{12''}$ are straight-chain, branched-chain or cyclic hydrocarbon groups having 1 to 30 carbon atoms, and, when $1+m+n=0$, at least one of $R^{1''}$ to $R^{3''}$ and $R^{10''}$ to $R^{12''}$ represents a group represented by general formula (2) and at least one of the remainings of $R^{1''}$ to $R^{3''}$ and $R^{10''}$ to $R^{12''}$ represents a group represented by general formula (3).

That is, an organohydrogen polysiloxane (4') having at least two silicon-hydrogen bondings is reacted with an alkenylglyceryl ether (2') and a compound (3') to obtain a siloxane derivative (1b) having a group represented by general formula (3). In this case, any of compounds (2') and (3') can be firstly reacted with compound (4'), or both compounds (2') and (3') can be reacted with compound (4') at the same time.

The organohydrogen polysiloxane (4) or (4') of the raw material essentially includes at least one [(4)] or two [(4')] silicon-hydrogen bonding or bondings in the molecule, but there is no further limitation in its viscosity, molecular structure and so forth. Hence, various kinds of known polysiloxanes can be used, but as to l, m and n, a range of 0 to 2000 is preferable in view of availability of raw materials of organohydrogen polysiloxanes, operability in manufacturing and the like.

As to compound (2'), a compound represented by general formula (2') wherein Q' is an ω-alkenyl group is preferable. Regarding compound (3'), a compound represented by general formula (3') wherein X' is CH2=CHCH2—(OC2H4)p—(OC3H6)q—O— (p and q are the same as described above), CH2=CH—(CH2)r'—O—CO— (r' is an integer of 1 to 18), CH2=CH—(CH2)r'—CO—O— (r' is the same as above), or the like is preferable.

In the above-described preparations (i) and (ii), the reaction is carried out in the presence of a catalyst. As examples of the catalyst, catalysts usually used in a hydrosililation, for example, a free radical initiator; photo-initiator; complex compounds of a metal such as ruthenium, rhodium, palladium, osmium, iridium, platinum or the like; these carried on a silica gel or alumina; and the like can be given. In particular, platinic chloride, Speier's reagent (isopropyl alcohol solution of platinic chloride) or the like are preferable. An amount of the catalyst used is a sufficient amount for promoting the reaction of the organohydrogen polysiloxane (4) or (4') with the alkenylglyceryl ether (2') and/or the compound (3') and thus is not restricted. A preferable amount the catalyst is a range of $10^{-6}$ to $10^{-1}$ mol per 1 mol of olefin used.

In the reaction, a use of a reaction solvent is not essential, but the reaction can be run in a suitable solvent if necessary. As regards the reaction solvent, it is not limited in particular as long as it does not inhibit the reaction, for example, hydrocarbon solvents such as pentane, hexane, cyclohexane and the like; benzene series solvents such as benzene, toluene, xylene and the like; ether solvents such as diethyl ether, diisopropyl ether and the like; alcohol solvents such as methanol, ethanol, isopropanol, butanol and the like; and the like can be given. When the alcohol solvent is used, a pH regulator such as potassium acetate or the like is preferably used for preventing or inhibiting a dehydrogenation reaction between Si—H and —OH, as disclosed in Japanese patent laid-open No. Sho 57-149290.

Relating to the amount of the alkenylglyceryl ether (2') and/or the compound (3') with reference to the organohydrogen polysiloxane (4) or (4') used in this reaction, as long as a sufficient amount of alkenylglyceryl ether (2') for including at least one silicon-connected glyceryl group (2) in the molecule of the obtained siloxane derivative is present, any amount of the other compound is used. However, when an oil solution of carbon system is emulsified by using the obtained compound (1), the sum unit number of the groups (2) and (3) is equal to or more than that of the remaining siloxanes. When an oil solution of silicon system is emulsified by using the obtained compound (1), the sum unit number of the groups (2) and (3) is preferably in a range of at most 1/5 of that of the remaining siloxanes.

The hydrosililation is run at 0° C. to 200° C., preferably 0° C. to 100° C. in consideration of the reaction speed, coloring of the obtained compound and so forth. The reaction time is preferably approximately 0.5 to 24 hours.

Thus the obtained siloxane derivatives (1) according to the present invention can be preferably used as components for cosmetic preparations, particularly emulsifiers. The formulations and kinds of the applicable cosmetic preparations can not be limited in particular, for instance, skin care cosmetic preparations such as milk lotion or liquid cream, lotion, foundation and the like; hair care cosmetic preparations such as shampoo, rinse, treatment and the like are given. A mixing amount of the siloxane derivative (1) of the present invention in the cosmetic preparation can not be also limited in particular, but usually a preferable amount is 0.001 to 90% by weight, more preferably 1 to 50% by weight in particular.

As described above, the siloxane derivatives (1) are useful as emulsifiers and can be mixed in a variety of emulsifying systems, and, when the siloxane derivatives are used in emulsifying dermatotherapeutic external agents in particular, stable external agents having good usage feeling can be obtained. Their preferable composition is as follows.

(A) oil phase component: 5 to 70 weight %, particularly preferably 10 to 50 weight %;

(B) water phase component: 20 to 94.9 weight %, particularly preferably 50 to 90 weight %; and (C) emulsifier including a siloxane derivative (1): 0.1 to 30 weight %, particularly preferably 0.5 to 30 weight %.

As to the oil phase component (A) used in the emulsifying dermatotherapeutic external agents, for example, silicone oils; hydrocarbons such as squalene, liquid paraffin, vaseline and the like; waxes such as spermaceti, carnauba wax and the like; ester oils such as jojoba oil, octyldodecyl myristate, neopentyl dioctanoate glycol and the like; natural animal or vegetable oils such as olive oil, macademia nut oil and the like; diglyceride and the like can be given. In these oils, as examples of the silicone oils, oils usually used in cosmetic preparations can be used, for example, dimethyl polysiloxane, dimethylcyclo polysiloxane, methylphenyl polysiloxane, methylhydrogen polysiloxane and the like can be given. Particularly, in order to reduce oiliness feeling and stickiness feeling, volatile dimethyl polysiloxane, dimethylcyclo polysiloxane and the like can be preferably exemplified. These oil solutions can be used independently or at least two kinds of the oil solutions can be used in combination.

The main ingredient (at least 50 weight %, and particularly at least 70 weight %) of the oil phase component (A) is the silicone oil, the obtained emulsifying dermatotherapeutic external agents possess plain usage feeling, and its emulsifying system is stable. In case that the silicone oil is the main ingredient as the oil phase component, a siloxane derivative represented by general formula (1) wherein l+m+n=0 to 2000, and Q is an alkylene group having 3 to 20 carbon atoms can be preferably used as the emulsifiers in particular.

Further, when the main ingredient of the oil phase component (A) is an oil solution except the silicone oils, preferably, the compound (1A) or (1D) can be used in view of the stability. When the compound (1D) is used, excellent external agents having no stimulus can be obtained.

As examples of the water phase component (B), for example, in addition to water, alcohols, polyols, inorganic salts, organic salts and the like can be given. In these components, the polyols are particularly useful because of wet-holding or humidifying property. Such polyols include, for example, propylene glycol, isoprene glycol (manufactured by Kurare Company), 1,3-butylene glycol, dipropylene glycol, glycerol, diglycerol, triglycerol, polyglycerol, trimethylolpropane, erythritol, pentaerythritol, sorbitan, sorbitol, glucose, maltitol, succharose, trehalose, ethylene oxide or propylene oxide adducts of sugar or sugar derivatives, polyethyleneglycol and the like. In particular, ethylene oxide adducts of the sugar derivatives such as glycerol, sorbitol, maltitol, polyoxyethylenemethyl glucoside and the like are preferable. These can be used independently or in combination. The mixing amount of the polyol is different depending on humidifying property, usage feeling, consistency and the like of the dermatotherapeutic external agents to be obtained, and, when an amount of 30 to 90 weight %, particularly 40 to 65 weight % of the polyol is mixed in the water phase, a difference of its refractive index with reference to the oil phase becomes small, and the appearance of the dermatotherapeutic external agents can be made to be semitransparent or transparent.

As to the inorganic salts or the organic salts, those having a solubility of at least 0.2 g/100 g of water at 20° C. are preferable. Such inorganic and organic salts include, for example, alkali metal salts, alkaline earth metal salts or aluminum salts of inorganic acids such as hydrochloric acid, sulfuric acid, nitric acid and the like; oxycarboxylic acids such as citric acid, tartaric acid, lactic acid, malic acid and the like; carboxylic acids such as formic acid, acetic acid, sorbic acid and the like; aromatic carboxylic acids such as salicylic acid, benzoic acid and the like.

As examples of the preferable inorganic and organic salts, for example, potassium sulfate, sodium sulfate, magnesium sulfate, aluminum sulfate, potassium nitrate, sodium nitrate, magnesium nitrate, aluminum nitrate, calcium nitrate, potassium chloride, magnesium chloride, sodium chloride, calcium chloride, aluminum chloride, potassium carbonate, sodium carbonate, aluminum carbonate, potassium acetate, sodium acetate, calcium acetate, magnesium acetate, sodium formate, potassium formate, magnesium formate, sodium citrate, sodium tartarate, potassium sorbate, sodium sorbate, sodium salicylate, sodium benzoate and the like are given. In particular, potassium sulfate, magnesium sulfate, potassium chloride, magnesium chloride, aluminum chloride, sodium citrate, sodium tartarate, potassium sorbate, sodium salicylate and sodium benzoate are more preferable.

These inorganic or organic salts can be mixed in the form of the salt in the external agents, or, when the external agent is produced, an acidic or basic material corresponding to the salt in a stoichiometric amount required for producing the salt can be added.

In the emulsifying dermatotherapeutic external agents according to the present invention, as regards the emulsifier (C), for example, in addition to the siloxane derivatives, surfactants having an emulsifier such as sorbitan fatty acid ester, glycerol fatty acid ester, polyoxyethylene hardened castor oil, isostearylglyceryl ether and the like can be used. A mixing amount of the emulsifier (C) is preferably 0.1 to 30 weight % per all amount of the emulsifying dermatotherapeutic external agent of the present invention, and 50 to 100 weight % of the siloxane derivative (1) is preferably mixed in this emulsifier (C).

In the emulsifying dermatotherapeutic external agent of the present invention, further 0 to 40 weight % of other ingredients used for usual dermatotherapeutic external agents can be suitably mixed so far as they do not lose and reduce the effects of the present invention. As examples of the other ingredients, for example, powders, humectants, intercellular lipids (ceramides), ultraviolet radiation absorbers, alcohols, chelates, pH regulators, preservatives, thickeners, pigments, perfumes, medicinal effect ingredients and the like can be given.

In these ingredients, by mixing 10 to 40 weight %, preferably 15 to 30 weight % of powder in the emulsifying dermatotherapeutic external agent of the present invention, a liquefied or creamy foundation can be formed. Regarding the powders, powders generally used for cosmetic preparations, for example, extenders such as talc, mica, kaolin, cericite and the like; inorganic pigments such as titanium oxide, zinc oxide, iron oxide, ultramarine blue and the like; titanium mica type Pal's pigments; organic pigments or lakes such as blue color #404, red color #202, yellow color #401 and the like can be given. According to the present invention, at least one kind of powder can be freely selected for the use.

As to the emulsifying dermatotherapeutic external agents according to the present invention, skin cosmetic preparations such as face care creams or milk lotions, skin care creams or milk lotions, liquefied or creamy foundations and the like; hair cosmetic preparations; external drugs and the like are given.

EXAMPLES

Now, the present invention will be described in detail with reference to the exemplary embodiments, and it should be understood that these embodiments are given for only illustration of the invention and are not intended to be limitative therefor.

EXAMPLE 1

(1) Into a 100 ml two-necked or Claisen flask provided with a condenser and a magnetic stirrer, 97 g (0.72 mol) of 1,1,3,3-tetramethyldisiloxane and 30 g (0.36 mol) of 1-hexene were put, and 0.72 g (7.2 mmol) of 5% isopropyl alcohol solution of platinic chloride was added to the mixture solution to stir for 16 hours in an iced water bath. The solution was distilled to obtain 52.8 g of transparent colorless liquid (bp: 55° to 61° C./4 Torr) in a 67% yield. The obtained product was analyzed by IR and NMR spectra to confirm 1-hexyl-1,1,3,3-tetramethyldisiloxane.

(2) Into a 100 ml two-necked flask provided with a condenser and a magnetic stirrer, 15 g (69 mmol) of 1-hexyl-1,1,3,3-tetramethyldisiloxane obtained in (1), 12 g (91 mmol) of allylglyceryl ether, 1.8 g (1.8 mmol) of 19% ethanol solution of potassium acetate and 24 g of isopropyl alcohol were put, and 0.18 g (0.017 mmol) of 5% isopropyl alcohol solution of platinic chloride was added to the mixture solution to stir for 17 hours at 40° C. After removing the solvent of the solution by distillation, the reaction product was refined by a silica gel column to obtain 22 g of transparent colorless liquid in a 93% yield. The obtained product was analyzed by IR and NMR spectra to confirm 3-(3-hexyl-1,1,3,3-tetramethyldisiloxanyl)propylglyceryl ether (A). The result of the analysis of the compound was as follows.

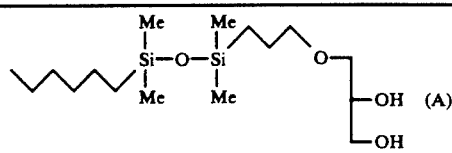

IR (liquid film, cm$^{-1}$)  3400 (—OH)
2928 (C—H)
1256 (Si—Me)
1064, 842, 796 (Si—O—Si)

$^1$H-NMR (δ ppm, in CDCl$_3$, CHCl$_3$ standard (7.28 ppm))

-continued

| | | |
|---|---|---|
| 0.04, 0.06 | (s, 12H) | Si—C$H_3$ |
| 0.08–1.02 | (t, 3H) | —C$H_3$ |
| 1.14–1.46 | (br, 8H) | —C$H_2$— |
| 0.40–0.66 | (m, 4H) | Si—C$H_2$— |
| 1.48–1.72 | (m, 2H) | C$H_2$—CH$_2$—O |
| 3.32–3.59 | (m, 4H) | C$H_2$—O |
| 3.79–3.98 | (m, 1H) | C$H$—OH |
| 3.59–3.79 | (m, 2H) | C$H_2$—OH |
| 2.83–2.93 | (d, 1H) | CH—O$H$ |
| 2.46–2.59 | (dd, 1H) | CH$_2$—O$H$ |

$^{13}$C-NMR (δ ppm, in CDCl$_3$, CHCl$_3$ standard (77.2 ppm))

| | |
|---|---|
| 0.46, 0.53 | Si—$C$H$_3$ |
| 14.3, 14.4 | —$C$H$_3$, $C$H$_2$—CH$_2$—CH$_2$O |
| 22.8, 23.4, 23.6, 31.8, 33.2 | —$C$H$_2$— |
| 18.5 | Si—$C$H$_2$— |
| 64.4 | $C$H$_2$—OH |
| 70.7 | $C$H—OH |
| 72.5 | $C$H$_2$—$C$H$_2$—O |
| 74.6 | CH—$C$H$_2$—O |

$^{29}$Si-NMR (δ ppm, in CDCl$_3$, TMS standard (0 ppm))

7.22, 7.89

EXAMPLE 2

(1) 1-decyl-1,1,3,3-tetramethyldisiloxane was obtained in a 70% yield in the same manner as Example 1 (1).

(2) 3-(3-decyl-1,1,3,3-tetramethyldisiloxanyl)propylglyceryl ether (B) was obtained in a 93% yield in the same manner as Example 1 (2). The result of the analysis of the compound was as follows.

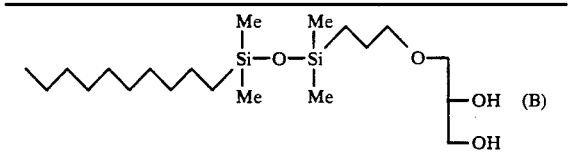

(B)

IR (liquid film, cm$^{-1}$)   3424 (—OH)
                  2928 (C—H)
                  1254 (Si—Me)
          1066, 840, 796 (Si—O—Si)

$^1$H-NMR (δ ppm, in CDCl$_3$, CHCl$_3$ standard (7.28 ppm))

| | | |
|---|---|---|
| 0.04, 0.06 | (s, 12H) | Si—C$H_3$ |
| 0.80–0.95 | (t, 3H) | —C$H_3$ |
| 1.15–1.42 | (br, 16H) | —C$H_2$— |
| 1.48–1.68 | (m, 2H) | C$H_2$—CH$_2$—O |
| 3.38–3.53 | (m, 4H) | C$H_2$—O |
| 0.38–0.57 | (m, 4H) | Si—C$H_2$— |
| 3.77–3.94 | (m, 1H) | C$H$—OH |
| 3.53–3.77 | (m, 2H) | C$H_2$—OH |
| 2.25–2.32 | (d, 1H) | CH—O$H$ |
| 2.98–3.08 | (t, 1H) | CH$_2$—O$H$ |

$^{13}$C-NMR (δ ppm, in CDCl$_3$, CHCl$_3$ standard (77.2 ppm))

| | |
|---|---|
| 0.42, 0.50 | Si—$C$H$_3$ |
| 14.2, 14.3 | —$C$H$_3$, $C$H$_2$—CH$_2$—CH$_2$O |
| 22.8, 23.4, 29.48, 29.53, 29.75, 29.81, 32.1, 33.6 | } —$C$H$_2$— |
| 18.5 | Si—$C$H$_2$— |
| 23.5 | $C$H$_2$—CH$_2$—O |
| 72.4 | CH$_2$—$C$H$_2$—O |
| 74.6 | CH—$C$H$_2$—O |
| 70.9 | $C$H—OH |
| 64.3 | $C$H$_2$—OH |

$^{29}$Si-NMR (δ ppm, in CDCl$_3$, TMS standard (0 ppm))

7.22, 7.89

EXAMPLE 3

(1) 1-hexadecyl-1,1,3,3-tetramethyldisiloxane was obtained in a 70% yield in the same manner as Example 1 (1).

(2) 3-(3-hexadecyl-1,1,3,3-tetramethyldisiloxanyl)-propylglyceryl ether (C) was obtained in a 93% yield in the same manner as Example 1 (2). The result of the analysis of the compound was as follows.

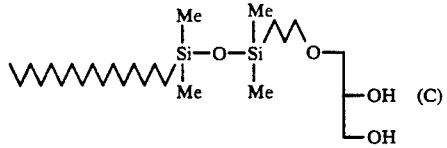

(C)

IR (liquid film, cm$^{-1}$)   3404 (—OH)
                  2956 (C—H)
                  1254 (Si—Me)
          1064, 840, 796 (Si—O—Si)

$^1$H-NMR (δ ppm, in CDCl$_3$, CHCl$_3$ standard (7.28 ppm))

| | | |
|---|---|---|
| 0.04, 0.06 | (s, 12H) | Si—C$H_3$ |
| 0.81–0.96 | (t, 3H) | —C$H_3$ |
| 1.16–1.41 | (br, 28H) | —C$H_2$— |
| 0.41–0.59 | (m, 4H) | Si—C$H_2$— |
| 1.53–1.70 | (m, 2H) | C$H_2$—CH$_2$—O |
| 3.36–3.59 | (m, 4H) | C$H_2$—O |
| 3.59–3.80 | (m, 2H) | C$H_2$—OH |
| 2.83–2.93 | (d, 1H) | CH—O$H$ |
| 2.46–2.59 | (dd, 1H) | CH$_2$—O$H$ |

$^{13}$C-NMR (δ ppm, CDCl$_3$, CHCl$_3$ standard (77.2 ppm))

| | |
|---|---|
| 0.47, 0.54 | Si—$C$H$_3$ |
| 14.3, 14.4 | —$C$H$_3$, $C$H$_2$—CH$_2$—CH$_2$O |
| 22.9, 23.5, 29.5, 29.6, 29.80, 29.84, 29.9, 32.1, 33.6 | } —$C$H$_2$— |
| 18.6 | Si—$C$H$_2$— |
| 23.6 | $C$H$_2$—CH$_2$—O |
| 64.4 | $C$H$_2$—OH |
| 70.7 | $C$H—OH |
| 72.6 | CH$_2$—$C$H$_2$—O |
| 74.6 | CH—$C$H$_2$—O |

$^{29}$Si-NMR (δ ppm, in CDCl$_3$, TMS standard (0 ppm))

7.22, 7.93

EXAMPLE 4

Into a 100 ml two-necked flask provided with a condenser and a magnetic stirrer, 20 g (30 mmol) of nonadecamethylnonasiloxane, 9.5 g (39 mmol) of 10-undecenylglyceryl ether, 0.77 g (0.78 mmol) of 10% ethanol solution of potassium acetate and 18.5 g of isopropyl alcohol were put, and 0.20 g (7.7×10$^{-3}$ mmol) of 2% isopropyl alcohol solution of platinic chloride was added to the mixture solution to heat the solution to raise its temperature. While the solution was kept to 40° C., the solution was stirred for 3.5 hours. After removing the solvent from the solution by distillation, the obtained reaction product was dissolved in hexane, and the solution was filtered. After removing the solvent from the solution, the obtained reaction product was refined by a silica gel column to obtain 21.7 g of transparent colorless oil in a 80% yield. The obtained product was analyzed by IR and NMR spectra to confirm nonadecamethylnonasiloxanylundecylglyceryl ether (D). The result of the analysis of the compound was as follows.

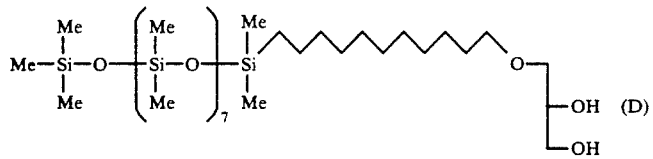

(D)

<u>$^1$H-NMR (δ ppm, in CDCl$_3$, CHCl$_3$ standard (7.28 ppm))</u>

| | | |
|---|---|---|
| 0.00–0.18 | (m, 57H) | Si—C$\underline{H}_3$ |
| 0.48–0.64 | (m, 2H) | Si—C$\underline{H}_2$— |
| 1.20–1.42 | (br, 16H) | —C$\underline{H}_2$— |
| 1.50–1.68 | (m, 2H) | C$\underline{H}_2$—CH$_2$—O |
| 3.40–3.58 | (m, 4H) | C$\underline{H}_2$—O |
| 3.78–3.96 | (m, 1H) | C$\underline{H}$—OH |
| 3.58–3.78 | (m, 2H) | C$\underline{H}_2$—OH |
| 2.67–2.72 | (d, 1H) | CH—O$\underline{H}$ |
| 2.21–2.35 | (dd, 1H) | CH$_2$—O$\underline{H}$ |

<u>$^{13}$C-NMR (δ ppm, in CDCl$_3$, CHCl$_3$ standard (77.2 ppm))</u>

| | |
|---|---|
| 0.39, 1.26, 1.34, 1.37, 1.98 | Si—$\underline{C}$H$_3$ |
| 18.5 | Si—$\underline{C}$H$_2$— |
| 23.4, 26.3, 29.6, 29.7, 29.8, 29.9, 33.7 | —$\underline{C}$H$_2$— |
| 64.5 | $\underline{C}$H$_2$—OH |
| 70.7 | $\underline{C}$H—OH |
| 72.1 | CH$_2$—$\underline{C}$H$_2$—O |
| 72.7 | CH—$\underline{C}$H$_2$—O |

<u>$^{29}$Si-NMR (δ ppm, in CDCl$_3$, TMS standard (0 ppm))</u>

| | |
|---|---|
| 7.28, 7.60 | a, i |
| −21.4, −21.7, −21.9, −22.0, −22.1 | b, c, d, e, f, g, h |

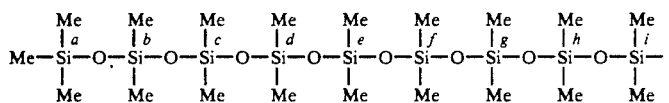

EXAMPLE 5

Pentamethyldisiloxanylundecylglyceryl ether (E) was obtained in a 56% yield in the same manner as Example 4. The result of the analysis of the compound was as follows.

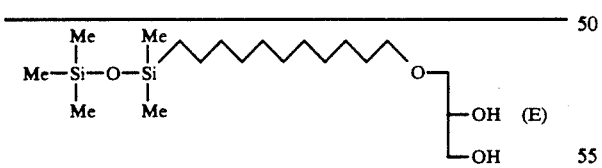

(E)

IR (liquid film, cm$^{-1}$)  3394 (—OH)
2926, 2860 (C—H)
1254 (Si—Me)
1062, 843 (Si—O—Si)

<u>$^1$H-NMR (δ ppm, in CDCl$_3$, CHCl$_3$ standard (7.28 ppm))</u>

| | | |
|---|---|---|
| 0.05, 0.07 | (s, 15H) | Si—C$\underline{H}_3$ |
| 0.43–0.62 | (m, 2H) | Si—C$\underline{H}_2$— |
| 1.14–1.40 | (br, 16H) | —C$\underline{H}_2$— |
| 1.50–1.68 | (m, 2H) | C$\underline{H}_2$—CH$_2$—O |
| 3.38–3.58 | (m, 4H) | C$\underline{H}_2$—O |
| 3.80–3.95 | (m, 1H) | C$\underline{H}$—OH |
| 3.58–3.80 | (m, 2H) | C$\underline{H}_2$—OH |
| 2.72–2.81 | (d, 1H) | CH—O$\underline{H}$ |
| 2.31–2.47 | (br, 1H) | CH$_2$—O$\underline{H}$ |

<u>$^{13}$C-NMR (δ ppm in CDCl$_3$, CHCl$_3$ standard (77.2 ppm))</u>

| | |
|---|---|
| 0.51, 2.14 | Si—$\underline{C}$H$_3$ |
| 18.6 | Si—$\underline{C}$H$_2$— |
| 23.4, 26.3, 29.6, 33.6 | —$\underline{C}$H$_2$— |
| 64.4 | $\underline{C}$H$_2$—OH |
| 70.7 | $\underline{C}$H—OH |
| 72.0 | CH—$\underline{C}$H$_2$—O |
| 72.6 | CH$_2$—$\underline{C}$H$_2$—O |

<u>$^{29}$Si-NMR (δ ppm, in CDCl$_3$, TMS standard (0 ppm))</u>

6.97, 7.61

EXAMPLE 6

Undecamethylpentasiloxanylundecylglyceryl ether (F) was obtained in a 48% yield in the same manner as Example 4. At this time, since 1,5-dihydrodecamethylpentasiloxane was included in a raw material of undecamethylpentasiloxane, 1,5-bis[11-(2,3-dihydroxypropoxy)undecyl]decamethylpentasiloxane (G) was obtained at the same time. The obtained compound (G) was isolated and refined by a silica gel column. The structures of the obtained products were confirmed by an analysis using IR and NMR spectra. The result of the analysis of the compounds was as follows.

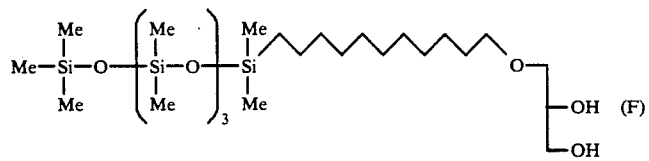

(F)

IR (liquid film, cm$^{-1}$)
3406 (—OH)
2962, 2926, 2860 (C—H)
1260 (Si—Me)
1035, 801 (Si—O—Si)

$^1$H-NMR (δ ppm, in CDCl$_3$, CHCl$_3$ standard (7.28 ppm))

| | | |
|---|---|---|
| −0.02–0.18 | (s, 33H) | Si—$\underline{CH_3}$ |
| 0.46–0.63 | (m, 2H) | Si—$\underline{CH_2}$— |
| 1.17–1.42 | (br, 16H) | —$\underline{CH_2}$— |
| 1.48–1.70 | (m, 2H) | $\underline{CH_2}$—CH$_2$—O |
| 3.38–3.59 | (m, 4H) | $\underline{CH_2}$—O |
| 3.77–3.97 | (m, 1H) | $\underline{CH}$—OH |
| 3.59–3.77 | (m, 2H) | $\underline{CH_2}$—OH |
| 2.83–2.98 | (d, 1H) | CH—$\underline{OH}$ |
| 2.46–2.64 | (br, 1H) | CH$_2$—$\underline{OH}$ |

$^{13}$C-NMR (δ ppm, in CDCl$_3$, CHCl$_3$ standard (77.2 ppm))

| | |
|---|---|
| 0.37, 1.94, 1.24, 1.32, 1.35 | Si—$\underline{C}$H$_3$ |
| 18.5 | Si—$\underline{C}$H$_2$— |
| 23.4, 26.3, 29.58, 29.66, 29.77, 29.84, 33.6 | —$\underline{C}$H$_2$— |
| 64.4 | $\underline{C}$H$_2$—OH |
| 70.7 | $\underline{C}$H—OH |
| 72.0 | $\underline{C}$H$_2$—CH$_2$—O |
| 72.7 | CH—$\underline{C}$H$_2$—O |

$^{29}$Si-NMR (δ ppm, in CDCl$_3$, TMS standard (0 ppm))

| | |
|---|---|
| 7.28, 7.61 | a, e |
| −21.4, −21.7, −22.2, | b, c, d |

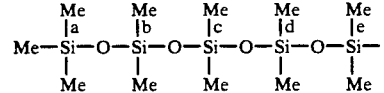

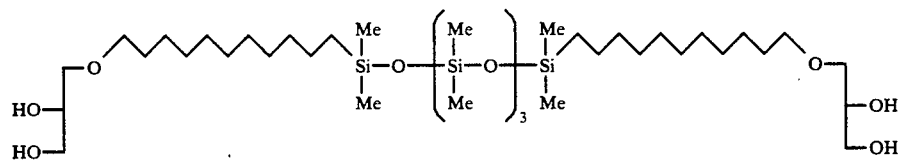

(G)

IR (liquid film, cm$^{-1}$)
3404 (—OH)
2924, 2856 (C—H)
1260 (Si—Me)
1080, 1034, 802 (Si—O—Si)

$^1$H-NMR (δ ppm, in CDCl$_3$, CHCl$_3$ standard (7.28 ppm))

| | | |
|---|---|---|
| 0.03, 0.05 | (s, 30H) | Si—$\underline{CH_3}$ |
| 0.54 | (t, 4H) | Si—$\underline{CH_2}$— |
| 1.28 | (br, 32H) | —$\underline{CH_2}$— |
| 1.48–1.69 | (m, 4H) | $\underline{CH_2}$—CH$_2$—O |
| 2.92 | (t, 2H) | $\underline{CH_2}$—OH |
| 3.20 | (d, 2H) | CH—$\underline{OH}$ |
| 3.36–3.57 | (m, 8H) | $\underline{CH_2}$—O |
| 3.57–3.78 | (m, 4H) | $\underline{CH_2}$—OH |
| 3.78–3.96 | (m, 2H) | $\underline{CH}$—OH |

$^{13}$C-NMR (δ ppm, in CDCl$_3$, CHCl$_3$ standard (77.2 ppm))

| | |
|---|---|
| 0.35, 1.34 | a, b |
| 1.24 | c |
| 18.4 | Si—$\underline{C}$H$_2$— |
| 23.4, 26.2, 29.56, 29.64, 29.73, 29.76, 29.8 | —$\underline{C}$H$_2$— |
| 64.4 | $\underline{C}$H$_2$—OH |
| 70.8 | $\underline{C}$H—OH |
| 72.0 | $\underline{C}$H$_2$—CH$_2$—O |
| 72.5 | CH—$\underline{C}$H$_2$—O |

$^{29}$Si-NMR (δ ppm, in CDCl$_3$, TMS standard (0 ppm))

| | |
|---|---|
| −22.3 | C |

| | |
|---|---|
| −21.7 | B |
| 78.62 | A |

EXAMPLE 7

Into a 100 ml two-necked flask provided with a condenser and a magnetic stirrer, 30 g (18.5 mmol) of α,ω-dihydromethylpolysiloxane (average chain length of 20), 11.8 g (48.3 mmol) of 10-undecenylglyceryl ether, 0.95 g (0.97 mmol) of 10% ethanol solution of potassium acetate and 24 g of isopropyl alcohol were put, and 0.26 g (0.010 mmol) of 2% isopropyl alcohol solution of platinic chloride was added to the mixture solution to heat the solution to raise its temperature. While the solution was kept to 50° C., the solution was stirred for 2 hours. After removing the solvent from the solution by distillation, unreacted 10-undecenylglyceryl ether was removed by vacuum distillation to obtain a brown high viscous material. This brown high viscous material was treated by active carbon to obtain 35.0 g of transparent colorless high viscous material in a 89.7% yield.

The obtained product was analyzed by IR and NMR spectra to confirm α,ω-bis[11-(2,3-dihydroxypropoxy)undecyl]dimethylpolysiloxane (average chain length of 20) (H). The result of the analysis of the compound was as follows.

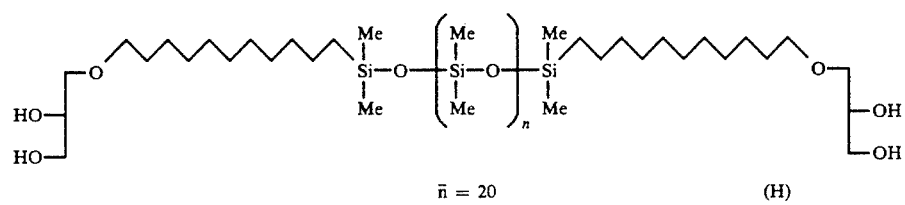

$\bar{n} = 20$ (H)

| IR (liquid film, cm$^{-1}$) | | |
|---|---|---|
| 3420 (—OH) | | |
| 2964, 2928, 2860 (C—H) | | |
| 1262 (Si—Me) | | |
| 1100, 1026, 802 (Si—O—Si) | | |
| $^1$H-NMR (δ ppm, in CDCl$_3$, CHCl$_3$ standard (7.28 ppm)) | | |
| 0.00 | (br, approx. 132H) | Si—CH$_3$ |
| 0.57 | (t, 4H) | Si—CH$_2$— |
| 1.39 | (br, 32H) | —CH$_2$— |
| 1.47–1.70 | (m, 4H) | CH$_2$—CH$_2$—O |
| 2.22 | (br, 2H) | CH$_2$—OH |
| 2.62 | (br, 2H) | CH—OH |
| 3.30–3.59 | (m, 8H) | CH$_2$—O |
| 3.59–3.80 | (m, 4H) | CH$_2$—OH |
| 3.80–3.96 | (m, 2H) | CH—OH |
| $^{13}$C-NMR (δ ppm, in CDCl$_3$, CHCl$_3$ standard (77.2 ppm)) | | |
| 0.39, 1.23, 1.36 | | Si—CH$_3$ |
| 18.5 | | Si—CH$_2$— |
| 23.4, 26.3, 29.6, 29.8, 33.7 | | —CH$_2$— |
| 64.7 | | CH$_2$—OH |
| 70.6 | | CH—OH |
| 72.0 | | CH$_2$—CH$_2$—O |
| 72.7 | | CH—CH$_2$—O |
| $^{29}$Si-NMR (δ ppm, in CDCl$_3$, TMS standard (0 ppm)) | | |

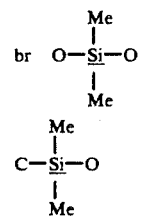

EXAMPLE 8

α,ω-bis[11-(2,3-dihydroxypropoxy)undecyl]dimethylpolysiloxane (average chain length of 50) (I) in a 95.3% yield in the same manner as Example 7. The result of the analysis of the compound was as follows.

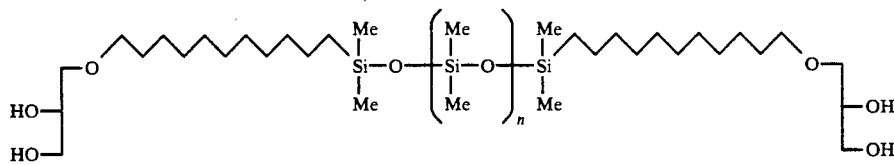

$\bar{n} = 50$     (I)

IR (liquid film, cm$^{-1}$)
- 3420 (—OH)
- 2968, 2932 (C—H)
- 1264 (Si—Me)
- 1094, 1020, 866, 802 (Si—O—Si)

$^1$H-NMR (δ ppm, in CDCl$_3$, CHCl$_3$ standard (7.28 ppm))

| | | |
|---|---|---|
| 0.08 | (br, approx. 312H) | Si—C$\underline{H}_3$ |
| 0.57 | (t, 4H) | Si—C$\underline{H}_2$— |
| 1.30 | (br, 32H) | —C$\underline{H}_2$— |
| 1.48–1.80 | (m, 4H) | C$\underline{H}_2$—CH$_2$—O |
| 2.20 | (br, 2H) | C$\underline{H}_2$—OH |
| 2.63 | (br, 2H) | CH—O$\underline{H}$ |
| 3.38–3.60 | (m, 8H) | C$\underline{H}_2$—O |
| 3.60–3.81 | (m, 4H) | C$\underline{H}_2$—OH |
| 3.81–3.97 | (m, 2H) | C$\underline{H}$—OH |

$^{13}$C-NMR (δ ppm, in CDCl$_3$, CHCl$_3$ standard (77.2 ppm))

| | |
|---|---|
| 0.38, 1.22, 1.36, 1.96 | Si—$\underline{C}$H$_3$ |
| 18.5 | Si—$\underline{C}$H$_2$— |
| 23.4, 26.3, 29.6, 29.8, 33.7 | —$\underline{C}$H$_2$— |
| 64.7 | $\underline{C}$H$_2$—OH |
| 70.8 | $\underline{C}$H—OH |
| 72.1 | $\underline{C}$H$_2$—CH$_2$—O |
| 72.7 | CH—$\underline{C}$H$_2$—O |

$^{29}$Si-NMR (δ ppm, in CDCl$_3$, TMS standard (0 ppm))

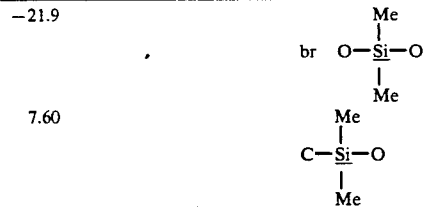

EXAMPLE 9

(1) Into a 100 ml two-necked flask provided with a condenser and a magnetic stirrer, 32.8 g (56.6 mmol) of α,ω-dihydrohexadecamethyldisiloxane and 4.0 g (28.5 mmol) of 1-decene were put, and 3.0 mg (5.8×10$^{-3}$ mmol) of platinic chloride was added to the mixture solution to stir for 6 hours in a water bath. The solution was distilled to obtain 11.0 g of transparent colorless liquid (bp: 160° C./0.005 Torr) in a 54% yield. The obtained product was analyzed by IR and NMR spectra to confirm 1-decyl-15-hydrohexadecamethyloctasiloxane.

(2) Into a 100 ml two-necked flask provided with a condenser and a magnetic stirrer, 10 g (13.9 mmol) of 1-decyl-15-hydrohexadecamethyloctasiloxane obtained in (1), 4.4 g (18.0 mmol) of 10-undecenylglyceryl ether, 0.35 g (0.36 mmol) of 10% ethanol solution of potassium acetate and 10 g of isopropyl alcohol were put, and 0.093 g (3.6×10$^{-3}$ mmol) of 2% isopropyl alcohol solution of platinic chloride was added to the mixture solution to heat the solution to raise its temperature. While the solution was kept to 40° C., the solution was stirred for 3 hours. After removing the solvent from the solution by distillation, the reaction product was refined by a silica gel column to obtain 11.8 g of transparent colorless oil in a 88% yield. The obtained product was analyzed by IR and NMR spectra to confirm 15-decylhexadecamethyloctasiloxanylundecylglyceryl ether (J). The result of the analysis of the compound was as follows.

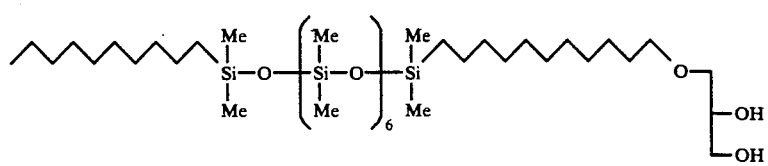

(J)

IR (liquid film, cm$^{-1}$)
- 3400 (—OH)
- 2964, 2928, 2860 (C—H)

| | | |
|---|---|---|
| | 1262 (Si—Me) | |
| | 1096, 1026, 840, 804 (Si—O—Si) | |
| ¹H-NMR (δ ppm, in CDCl₃, CHCl₃ standard (7.28 ppm)) | | |
| −0.02–0.10 | (m, 48H) | Si—C$\underline{H}_3$ |
| 0.50 | (t, 4H) | Si—C$\underline{H}_2$— |
| 0.87 | (t, 3H) | —C$\underline{H}_3$ |
| 1.24 | (br, 32H) | —C$\underline{H}_2$— |
| 1.47–1.66 | (m, 2H) | C$\underline{H}_2$—CH$_2$—O |
| 2.32 | (t, 1H) | CH$_2$—O$\underline{H}$ |
| 2.71 | (d, 1H) | CH—O$\underline{H}$ |
| 3.36–3.57 | (m, 4H) | C$\underline{H}_2$—O |
| 3.57–3.78 | (m, 2H) | C$\underline{H}_2$—OH |
| 3.73–3.90 | (m, 1H) | C$\underline{H}$—OH |
| ¹³C-NMR (δ ppm, in CDCl₃, CHCl₃ standard (77.2 ppm)) | | |
| 0.38, 1.25, 1.35 | | Si—$\underline{C}$H$_3$ |
| 14.3 | | —$\underline{C}$H$_3$ |
| 18.5 | | Si—$\underline{C}$H$_2$— |
| 22.9, 23.4, 26.3, 29.5, 29.6, 29.7, 29.8, 29.9, 32.1 | } | —$\underline{C}$H$_2$— |
| 64.5 | | $\underline{C}$H$_2$—OH |
| 70.7 | | $\underline{C}$H—OH |
| 72.1 | | CH$_2$—$\underline{C}$H$_2$—O |
| 72.7 | | CH—$\underline{C}$H$_2$—O |

EXAMPLE 10

Into a 100 ml two-necked flask provided with a condenser and a magnetic stirrer, 15 g (4.4 mmol) of organohydrogen siloxane represented by the following formula (K'),

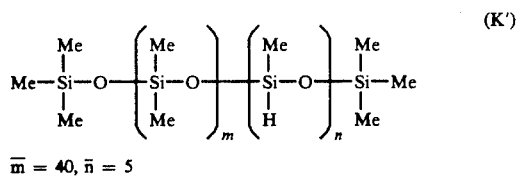

$\overline{m} = 40, \overline{n} = 5$ 8.1 g (33 mmol) of 10-undecenylglyceryl ether, 0.65 g (0.66 mmol) of 10% ethanol solution of potassium acetate and 50 g of isopropyl alcohol were put, and 0.17 g (6.6×10⁻³ mmol) of 2% isopropyl alcohol solution of platinic chloride was added to the mixture solution to heat the solution to raise its temperature. While the solution was kept to 40° C., the solution was stirred for 2.5 hours. After removing the solvent from the solution by distillation, the solid was treated by active carbon, and unreacted 10-undecenylglyceryl ether was removed by vacuum distillation to obtain a brown high viscous material. The obtained product was analyzed by IR and NMR spectra to confirm a compound represented by the following formula (K). The result of the analysis of the compound was as follows.

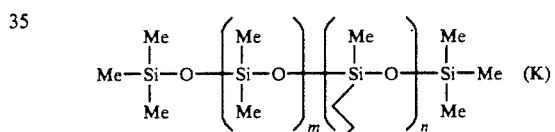

$\overline{m} = 40, \overline{n} = 5$

| IR (liquid film, cm⁻¹) | | |
|---|---|---|
| 3400 (—OH) | | |
| 2968, 2932, 2860 (C—H) | | |
| 1262 (Si—Me) | | |
| 1096, 1022, 844 (Si—O—Si) | | |
| ¹H-NMR (δ ppm, in CDCl₃, CHCl₃ standard (7.28 ppm)) | | |
| 0.01 | (s, approx. 273H) | Si—C$\underline{H}_3$ |
| 0.38–0.58 | (m, 10H) | Si—C$\underline{H}_2$— |
| 1.10–1.41 | (br, 80H) | —C$\underline{H}_2$— |
| 1.44–1.86 | (m, 10H) | C$\underline{H}_2$—CH$_2$—O |
| 3.30–3.55 | (m, 20H) | C$\underline{H}_2$—O |
| 3.55–3.77 | (m, 10H) | C$\underline{H}_2$—OH |
| 3.77–3.90 | (m, 5H) | C$\underline{H}$—OH |

EXAMPLE 11

A compound represented by the following formula (L) was obtained in a 97% yield in the same manner as Example 10. The result of the analysis of the compound was as follows.

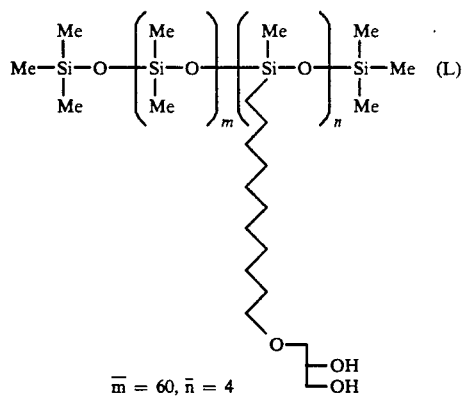

$\overline{m} = 60, \overline{n} = 4$

IR (liquid film, cm$^{-1}$)
3420 (—OH)
2968, 2932, 2860 (C—H)
1264 (Si—Me)
1096, 1026, 802 (Si—O—Si)

$^1$H-NMR (δ ppm, in CDCl$_3$, CHCl$_3$ standard (7.28 ppm))

| | | |
|---|---|---|
| 0.00 | (s, approx. 390H) | Si—CH$_3$ |
| 0.35–0.50 | (m, 8H) | Si—CH$_2$— |
| 1.08–1.39 | (br, 64H) | —CH$_2$— |
| 1.39–1.62 | (br, 8H) | CH$_2$—CH$_2$—O |
| 1.96–2.29 | (br, 4H) | CH$_2$—OH |
| 2.43–2.68 | (br, 4H) | CH—OH |
| 3.38–3.50 | (m, 16H) | CH$_2$—O |
| 3.50–3.70 | (m, 8H) | CH$_2$—OH |
| 3.70–3.86 | (m, 4H) | CH—OH |

EXAMPLE 12

A compound represented by the following formula (M) was obtained in a 99% yield in the same manner as Example 10. The result of the analysis of the compound was as follows.

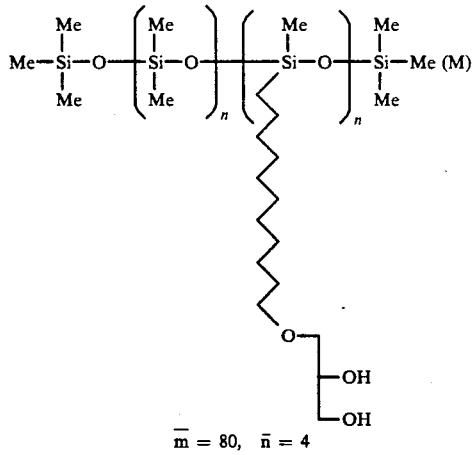

$\overline{m} = 80, \overline{n} = 4$

IR (liquid film, cm$^{-1}$) 3424 (—OH)
2964, 2928, 2860 (C—H)
1262 (Si—Me)
1096, 1034, 864, 798 (Si—O—Si)

$^1$H-NMR (δ ppm, in CDCl$_3$, CHCl$_3$ standard (7.28 ppm))

| | | |
|---|---|---|
| 0.00 | (s, approx. 510H) | Si—CH$_3$ |
| 0.34–0.55 | (m, 8H) | Si—CH$_2$— |
| 1.02–1.38 | (br, 64H) | —CH$_2$— |
| 1.38–1.66 | (br, 8H) | CH$_2$—CH$_2$—O |
| 1.98–2.40 | (br, 4H) | CH$_2$—OH |
| 2.40–2.78 | (br, 4H) | CH—OH |
| 3.26–3.53 | (m, 16H) | CH$_2$—O |
| 3.53–3.70 | (m, 8H) | CH$_2$—OH |
| 3.70–3.88 | (m, 4H) | CH—OH |

EXAMPLE 13

Into a 100 ml two-necked flask provided with a condenser and a magnetic stirrer, 10 g (7.5 mmol) of organohydrogen siloxane represented by the following formula (N')

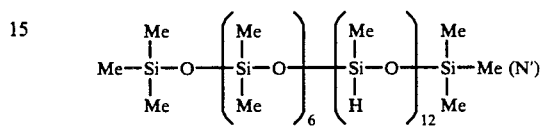

and 8.4 g (60.2 mmol) of decene were put, and 8.3×10$^{-3}$ ml of 2% isopropyl alcohol solution of platinic chloride was added to the mixture solution to heat the solution to 40° C. After 20 minutes, 20 g of isopropyl alcohol, 4.6 g (35 mmol) of allylglyceryl ether, 0.44 g of 10% ethanol solution of potassium acetate and 0.12 ml of 2% isopropyl alcohol solution of platinic chloride were added to the solution to heat to 40° C. After 2 hours, the isopropyl alcohol was removed by distillation. After the solution was treated by active carbon, and unreacted allylglyceryl ether was removed by vacuum distillation to obtain 22 g of colorless viscous material. The obtained product was analyzed by IR and NMR spectra to confirm a compound represented by the following formula (N). The result of the analysis of the compound was as follows.

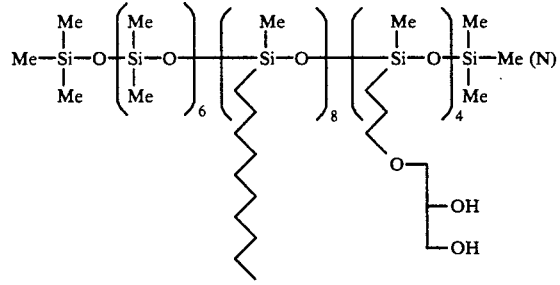

IR (liquid film, cm$^{-1}$) 3400 (—OH)
2965, 2925, 2860 (C—H)
805, 850, 1260 (Si—Me)
1090, 1030 (Si—O—Si)

$^1$H-NMR (δ ppm, in CDCl$_3$, CHCl$_3$ standard (7.28 ppm))

| | | |
|---|---|---|
| 0.06–0.11 | (bs, 90H) | Si—CH$_3$ |
| 0.51 | (m, 24H) | Si—CH$_2$—CH$_2$— |
| 0.90 | (t, 24H) | —CH$_2$—CH$_3$ |
| 1.28 | (br, 136H) | —CH$_2$— |
| 1.64–1.68 | (br, 8H) | —OH |
| 3.44–3.87 | (m, 28H) | —CH$_2$—O—, —CH—O—<br>                     \|<br>                     CH$_2$— |

EXAMPLE 14

22 g of compound represented by the following formula (O) was obtained in the same manner as Example 13 except that 11.7 g (83 mmol) of decene and 1.1 g (8.3 mmol) of allylglyceryl ether were used. The result of the analysis of the compound was as follows.

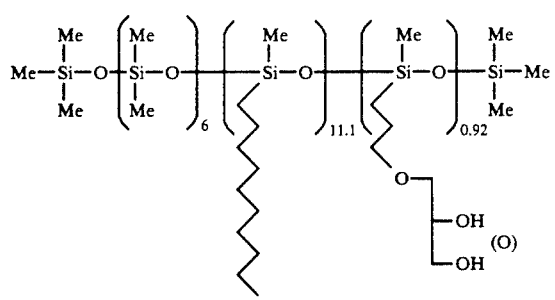

IR (liquid film, cm$^{-1}$)  3425 (—OH)
2970, 2930, 2865 (C—H)
805, 845, 1260 (Si—Me)
1095, 1025 (Si—O—Si)

$^1$H-NMR (δ ppm, in CDCl$_3$, CHCl$_3$ standard (7.28 ppm))
| | | |
|---|---|---|
| 0.06–0.12 | (bs, 90H) | Si—C$\underline{H}_3$ |
| 0.50 | (m, 24H) | Si—C$\underline{H}_2$—CH$_2$— |
| 0.90 | (t, 33.2H) | —CH$_2$—C$\underline{H}_3$ |
| 1.28 | (br, 179.1H) | —C$\underline{H}_2$— |
| 1.62–1.67 | (br, 1.8H) | —O$\underline{H}$ |
| 3.45–3.88 | (m, 6.5H) | —C$\underline{H}_2$—O—, —C$\underline{H}$—O— CH$_2$— |

EXAMPLE 15

Creamy Transparent or Semitransparent Emulsified Compositions

Emulsified compositions having compositions shown in Table 1 were prepared, and appearance and emulsification stability of each emulsified composition were evaluated right after preparation thereof, as shown in Table 1.

Preparation Method

First, ingredients (1) to (3) were mixed, and then, while stirring the mixture by an emulsifying apparatus, previously mixed ingredients (4) to (8) were gradually added to the mixture to carry out the emulsification to obtain emulsified compositions.

Emulsification Stability Evaluation Method

The obtained emulsified compositions were preserved at 25° C., and their appearance was observed after one month to evaluate the emulsification stability according to the following standard.
O: there is no change in state, good
Δ: there is slight separation and/or aggregation
X: there is separation and/or aggregation, insufficient emulsification

TABLE 1

(wt %)

| Components | Inventive composition | | | | | |
|---|---|---|---|---|---|---|
| | 1 | 2 | 3 | 4 | 5 | 6 |
| (1) Siloxane derivative (L) | 2 | 2 | 2 | 2 | 2 | 2 |
| (2) Dimethyl polysiloxane polyoxyalkylene copolymer* | | | | | | |
| (3) Dimethyl polysiloxane (50 cs) | 23 | 23 | 23 | 38 | 23 | 23 |
| (4) Glycerol | 30 | 39 | 48 | 30.8 | | |
| (5) 1,3-Butylene glycol | | | | | 39 | |
| (6) Sorbitol | | | | | | 39 |
| (7) Magnesium sulfate | 1 | 1 | 1 | 1 | 1 | 1 |
| (8) Purified water | 44 | 35 | 26 | 28.2 | 35 | 35 |
| Appearance | Semi-transparence | Transparence | Semi-transparence | Transparence | Transparence | Transparence |
| Emulsion stability | O | O | O | O | O | O |

| Components | Comparative composition | | | | | |
|---|---|---|---|---|---|---|
| | 1 | 2 | 3 | 4 | 5 | 6 |
| (1) Siloxane derivative (L) | | | | | | |
| (2) Dimethyl polysiloxane polyoxyalkylene copolymer* | 2 | 2 | 2 | 2 | 2 | 2 |
| (3) Dimethyl polysiloxane (50 cs) | 23 | 23 | 23 | 38 | 23 | 23 |
| (4) Glycerol | 30 | 39 | 48 | 30.8 | | |
| (5) 1,3-Butylene glycol | | | | | 39 | |
| (6) Sorbitol | | | | | | 39 |
| (7) Magnesium sulfate | 1 | 1 | 1 | 1 | 1 | 1 |
| (8) Purified water | 44 | 35 | 26 | 28.2 | 35 | 35 |
| Appearance | Semi- | Trans- | Semi- | Trans- | Trans- | Trans- |

TABLE 1-continued

|  | | | | | | (wt %) |
|---|---|---|---|---|---|---|
|  | trans-parence | parence | trans-parence | parence | parence | parence |
| Emulsion stability | Δ | X | X | X | X | X |

*Toray Silicone SH3775C (manufactured by Toray Silicone Co.)

As apparent from Table 1, the emulsified compositions of the present invention exhibited extremely excellent emulsification states. However, in the comparative compositions, an oil phase separation to an upper layer occurred with the passage of time and the comparative compositions are inferior in stability.

Further, emulsified compositions prepared by using another siloxane derivative (D), (F), (H), (I), (J), (K) or (M) in place of the siloxane derivative (L) used in the present compositions 1 to 6 in Table 1 also exhibit superior stability than the comparative compositions.

EXAMPLE 16

Creamy Emulsified Compositions

Emulsified compositions having compositions shown in Table 2 were prepared, and emulsification stability of each emulsified composition was evaluated, as shown in Table 2.

Preparation Method

First, ingredients (1) to (3) were mixed, and then, while stirring the mixture by an emulsifying apparatus, previously mixed ingredients (4) to (6) were gradually added to the mixture to carry out the emulsification to obtain emulsified compositions.

TABLE 2

|  | Composition of the Invention | | Comparative composition | | (wt %) |
|---|---|---|---|---|---|
| Components | 7 | 8 | 7 | 8 |  |
| (1) Siloxane derivative (M) | 2 | 2 |  |  |  |
| (2) Dimethyl polysiloxane polyoxyalkelene copolymer* |  |  | 2 | 2 |  |
| (3) Dimethyl polysiloxane (50 cs) | 23 | 23 | 23 | 23 |  |
| (4) Glycerol | 64 | 23 | 64 | 23 |  |
| (5) Magnesium sulfate | 1 | 1 | 1 | 1 |  |
| (6) Purified water | 10 | 51 | 10 | 51 |  |
| Emulsion stability | O | O | X | X |  |

*Silicone X-22-4013 (manufactured by Sinetsu Co.)

Emulsification Stability Evaluation Method

The obtained emulsified compositions were evaluated in the same manner as Example 15.

As apparent from Table 2, the emulsified compositions of the present invention exhibited extremely excellent emulsification states. However, in the comparative compositions, an oil phase separation to an upper layer occurred with the passage of time and their stability was inferior.

Further, emulsified compositions prepared by using another siloxane derivative (D), (F), (H), (I), (J), (K) or (L) in place of the siloxane derivative (M) used in the present compositions 7 and 8 in Table 2 also exhibit superior stability than the comparative compositions.

EXAMPLE 17

Hand Cream

| (Compositions) | (weight %) |
|---|---|
| (1) siloxane derivative (L) | 2.0 |
| (2) methylphenylpolysiloxane | 5.0 |
| (3) decamethylcyclopentasiloxane | 5.0 |
| (4) dimethylpolysiloxane (50 cs) | 10.0 |
| (5) pefume | 0.2 |
| (6) glycerol | 20.0 |
| (7) 1,3-butylene glycol | 15.0 |
| (8) magnesium sulfate | 1.0 |
| (9) purified water | 41.8 |

Preparation

First, ingredients (1) to (5) were mixed, and then, while stirring the mixture by an emulsifying apparatus, previously mixed ingredients (6) to (9) were gradually added to the mixture to carry out the emulsification to obtain a hand cream.

EXAMPLE 18

Wet-Holding Cream

| (Compositions) | (weight %) |
|---|---|
| (1) dimethylpolysiloxane (50 cs) | 10.0 |
| (2) decamethylcyclopentasiloxane | 5.0 |
| (3) squalene | 8.0 |
| (4) siloxane derivative (I) | 2.0 |
| (5) isostearylglyceryl ether | 1.0 |
| (6) glycerol | 20.0 |
| (7) 1,3-butylene glycol | 5.0 |
| (8) sorbitol | 5.0 |
| (9) magnesium sulfate | 1.0 |
| (10) perfume | 0.2 |
| (11) purified water | 41.8 |

Preparation

First, ingredients (1) to (5) and (10) were mixed, and then, while stirring the mixture by an emulsifying apparatus, previously mixed ingredients (6) to (9) and (11) were gradually added to the mixture to carry out the emulsification to obtain a wet-holding cream.

EXAMPLE 19

Creamy Foundation

| (Compositions) | (weight %) |
|---|---|
| (1) siloxane derivative (L) | 2.0 |
| (2) dimethylpolysiloxane (50 cs) | 10.0 |
| (3) octamethylcyclotetrasiloxane | 8.0 |
| (4) perfume | 0.2 |
| (5) silicone-treated cosmetic preparation powder* | 15.0 |
| (6) glycerol | 30.0 |
| (7) magnesium sulfate | 1.0 |

-continued

| (Compositions) | (weight %) |
|---|---|
| (8) purified water | 33.8 |

*the cosmetic preparation powder having the following composition was used as raw powder material. Before using this cosmetic preparation powder, the powder was added by 2% methylhydorogen polysiloxane {KF99 (Trade Name) manufactured by Shinetsu Silicone Co., Ltd.}, and the mixture was heat-treated.

Cosmetic Preparation Powder Composition

| (1) titanium oxide | 8 (parts by weight) |
|---|---|
| (2) talc | 4 |
| (3) red iron oxide | 1.2 |
| (4) yellow iron oxide | 2.6 |
| (5) black iron oxide | 0.2 |

Preparation

First, ingredients (1) to (4) were mixed, and then after adding ingredient (5) in the mixture to disperse therein, while stirring the mixture by an emulsifying apparatus, previously mixed ingredients (6) to (8) were gradually added to the mixture to carry out the emulsification to obtain a creamy foundation.

EXAMPLE 20

Suntan Cream

| (Compositions) | (weight %) |
|---|---|
| (1) siloxane derivative (J) | 5.0 |
| (2) dimethylpolysiloxane 50 cs) | 15.0 |
| (3) methylphenylpolysiloxane | 5.0 |
| (4) p-dimethylaminobenzoic acid** | 5.0 |
| (5) oxybenzone | 0.5 |
| (6) perfume | 0.2 |
| (7) glycerol | 8.0 |
| (8) 1,3-butylene glycol | 15.0 |
| (9) glucose | 2.0 |
| (10) sodium chloride | 1.0 |
| (11) purified water | balance |

**Escalol 507 (Trade Name) (manufactured by Van Dike Co., Ltd.)

Preparation

First, ingredients (1) to (6) were mixed, and then, while stirring the mixture by an emulsifying apparatus, previously mixed ingredients (7) to (11) were gradually added to the mixture to carry out the emulsification to obtain a suntan cream.

The emulsified cosmetic preparations of Examples 17 to 20 were all stable and extremely superior in wet-holding property, usage feeling or the like.

EXAMPLE 21

Emulsification Stabilizing Effect

Cosmetic preparation bases are prepared from the following compositions including siloxane derivative (N) or (G) or conventional emulsifiers as compounds to be examined, and their emulsification stability are tested, as shown in Table 3.

| Compositions: | |
|---|---|
| (1) liquid paraffin | 5 (parts by weight) |
| (2) purified water | 94 |
| (3) magnesium sulfate | 0.2 |
| (4) compound to be examined | 0.8 |

Preparation of Cosmetic Preparation Bases

To 5 parts by weight of liquid paraffin, 1 part by weight of sum of magnesium sulfate and a compound to be examined were added, and they were mixed and heated to 70° C. To this mixture, 94 parts by weight of ion-exchanged or purified water previously heated to 70° C. was gradually added to carry out emulsification. After emulsification, while the mixture was stirred, the mixture was air-cooled to a room temperature to obtain a cosmetic preparation base.

TABLE 3

| Test composition | | Emulsion type | State (right after) | State (after 7 days) Demulsification of Oil phase | Demulsification of Aqueous phase |
|---|---|---|---|---|---|
| Compound of the Invention | Siloxane derivative (N) | W/O | Uniform cream | 0 | 0 |
| | Siloxane derivative (G) | W/O | Uniform cream | 0 | 0 |
| Comparative composition | α-monooleyl glyceryl ether | W/O | Slightly uniform cream | 90 | 70 |
| | α-monostearyl glyceryl ether | W/O | Slightly ununiform cream | 100 | 85 |
| | 2-hexadecyl-eicosyl α-monoglyceryl ether | — | Separation | 100 | 100 |
| | Sorbitan monooleate | W/O | Slightly ununiform cream | 54 | 81 |
| | Sorbitan sesquioleate | W/O | Slightly uniform cream | 21 | 36 |
| | Sorbitan monostearate | W/O | Ununiform cream | 90 | 100 |
| | Glycerol monooleate | W/O | Slightly ununiform cream | 15 | 32 |
| | Glycerol monostearate | W/O | Ununiform cream | 100 | 100 |
| | Polyoxyethylene (5) oleyl ether | O/W | Uniform cream | 0 | 15 |
| | Polyoxyethylene (7) sorbitol tetraoleate | W/O | Slightly ununiform cream | 26 | 79 |
| | Polyoxyethylene (20) sorbitan monostearate | O/W | Slightly ununiform cream | 0 | 15 |
| | Polyoxyethylene (5) sesqui-lauryl phosphate | O/W | Slightly ununiform cream | 0 | 21 |
| | Sodium stearyl sulfate | O/W | Slightly ununiform cream | 0 | 85 |

Oil phase separation rate: $= \frac{\text{separated oil phase amount (ml)}}{6 \text{ (ml)}} \times 100(\%)$ Water phase separation rate: $= \frac{\text{separated water phase amount (ml)}}{94 \text{ (ml)}} \times 100(\%)$ As apparent from the above-described results, from the compositions mixing with compounds of the present invention, water-in-oil type cosmetic preparation bases readily blending a lot of water could be obtained, and their emulsification stability was excellent. On the other hand, when the conventional emulsifiers were used, it was difficult to obtain water-in-oil type cosmetic preparation bases. Even when water-in-oil type cosmetic preparation bases could be produced, an oil or water component was separated, and no stable emulsified base could be obtained.

EXAMPLE 22

Cosmetic preparation bases are prepared from the following compositions including siloxane derivative (N) or (G) or conventional emulsifiers as compounds to be examined in the same manner as Example 21, and their emulsification stability are tested, as shown in Table 4.

| Compositions: | |
|---|---|
| (1) liquid paraffin | 12.0 (parts by weight) |
| (2) dimethylpolysiloxane (50 cs) | 11.0 |
| (3) magnesium sulfate | 1.0 |
| (4) compound to be examined | 2.0 |
| (5) purified water | 74.0 |

TABLE 4

| Test composition | | Emulsion type | State (after 5 days) |
|---|---|---|---|
| Composition of the Invention | Siloxane derivative (N) | W/O | Excellent |
| | Siloxane derivative (G) | W/O | Excellent |
| Comparative composition | α-Mono-isostearyl glyceryl ether | W/O | Separation of Oil phase (13%) |
| | Dimethyl polysiloxane polyoxyalkylene copolymer (Toray SH3775C) | W/O | Separation of Oil phase (40%) |
| | Glycerol monostearate | W/O | Separation of Oil phase (100%) |

As apparent from the above-described results, in case that the compounds of the present invention were used, even when a silicone was included in an oil phase, cosmetic preparation bases having excellent emulsification stability could be obtained.

EXAMPLE 23

Nourishing Cream

| (Compositions) | (weight %) |
|---|---|
| (1) siloxane derivative (O) | 2.0 |
| (2) potassium sulfate | 0.5 |
| (3) squalane | 4.0 |
| (4) liquid paraffin | 2.0 |
| (5) hexadecyl-2-ethylhexanoate | 2.0 |
| (6) potassium benzoate | 0.3 |
| (7) propylene glycol | 2.0 |
| (8) acetic acid dl-α-tocopherol | 0.1 |
| (9) perfume | 0.1 |
| (10) purified water | balance |

Preparation

First, ingredients (1) to (5) were mixed and heated to 75° C., and then, while stirring the mixture, previously mixed ingredients (6), (7) and (10) previously heated to 70° C. were gradually added to the mixture to carry out the emulsification. After the emulsification, the mixture was cooled to 60° C., and ingredients (8) and (9) were added to the mixture. Further, the mixture was air-cooled to a room temperature to obtain a nourishing cream.

The obtained nourishing cream was excellent in emulsification stability, and its usage feeling was also excellent.

Other nourishing creams obtained by mixing 0.5% of potassium chloride, magnesium chloride or magnesium nitrate in place of the potassium sulfate in the same manner as described above exhibited the same results.

EXAMPLE 24

Hand Cream

| (Compositions) | (weight %) |
|---|---|
| (1) siloxane derivative (B) | 1.5 |
| (2) aluminum chloride | 0.8 |
| (3) IPM (isopropyl myristate) | 4.5 |
| (4) dimethylpolysiloxane (50 cs) | 4.0 |
| (5) methyl p-oxybenzoate | 0.2 |
| (6) sorbitol | 10.0 |
| (7) purified water | balance |

Preparation

First, ingredients (1) to (4) were mixed and heated to 75° C., and then, while stirring the mixture, previously mixed ingredients (5) to (7) previously heated to 75° C. were gradually added to the mixture to carry out the emulsification. Then, the mixture was air-cooled to a room temperature to obtain a hand cream.

The obtained hand cream was excellent in emulsification stability for a long period of time, and its usage feeling was also excellent. Also, the hand cream possesses water repellency and exhibited superior properties.

EXAMPLE 25

Cold Cream (Water-in-Oil Type)

| (Compositions) | (weight %) |
|---|---|
| (1) siloxane derivative (N) | 5.5 |
| (2) sodium nitrate | 1.0 |
| (3) liquid paraffin | 10.0 |
| (4) oleyl alcohol | 1.0 |
| (5) potassium sorbate | 0.2 |
| (6) glycerol | 5.0 |
| (7) perfume | 0.1 |
| (8) purified water | balance |

Preparation

First, ingredients (1) to (4) were mixed and heated to 75° C., and then, while stirring the mixture, previously mixed ingredients (5), (6) and (8) previously heated to 75° C. were gradually added to the mixture to carry out the emulsification. After cooling the mixture, an ingredient (7) was added to the mixture to obtain a cold cream.

The obtained cold cream exhibited excellent emulsification stability.

EXAMPLE 26

Vanishing Cream (Water-in-Oil Type)

| (Compositions) | (weight %) |
|---|---|
| (1) siloxane derivative (C) | 2.0 |
| (2) aluminum monostearate | 0.2 |
| (3) calcium chloride | 0.4 |
| (4) stearic acid | 1.0 |
| (5) glycerol tri-2-ethylhexanoate | 7.0 |
| (6) propyl p-oxybenzoate | 0.2 |
| (7) sorbitol | 5.0 |
| (8) perfume | 0.2 |
| (9) purified water | balance |

Preparation

First, ingredients (1) to (6) were mixed and heated to 75° C., and then, while stirring the mixture, previously mixed ingredients (7) and (9) previously heated to 75° C. were gradually added to the mixture to carry out the emulsification. After cooling the mixture, an ingredient (8) was added to the mixture to obtain a vanishing cream.

The obtained vanishing cream was excellent in emulsification stability for a long period of time, and its usage feeling was also excellent.

EXAMPLE 27

Cleansing Cream (Water-in-Oil Type)

| (Compositions) | (weight %) |
|---|---|
| (1) siloxane derivative (E) | 2.0 |
| (2) aluminum monopalmitate | 0.1 |
| (3) sodium citrate | 0.7 |
| (4) glycerol monooleate | 2.5 |
| (5) liquid paraffin | 12.0 |
| (6) bleached beeswax | 1.0 |
| (7) petrolatum | 1.0 |
| (8) di-2-ethylhexyladipate | 17.0 |
| (9) butyl p-oxybenzoate | 0.2 |
| (10) dibutylhydoxytoluene | 0.01 |
| (11) glycerol | 2.0 |
| (12) perfume | 0.2 |
| (13) purified water | balance |

Preparation

First, ingredients (1) to (10) were mixed and heated to 75° C., and then, while stirring the mixture, previously mixed ingredients (11) and (13) previously heated to 75° C. were gradually added to the mixture to carry out the emulsification. After cooling the mixture, an ingredient (12) was added to the mixture to obtain a cleansing cream.

The obtained cleansing cream was excellent in emulsification stability for a long period of time, and its usage feeling was also excellent.

EXAMPLE 28

Milk Lotion (Water-in-Oil Type)

| (Compositions) | (weight %) |
|---|---|
| (1) siloxane derivative (N) | 2.0 |
| (2) sodium tartarate | 1.5 |
| (3) sorbitan sesquioleate | 2.0 |
| (4) stearic acid | 1.5 |
| (5) olive oil | 4.0 |
| (6) liquid paraffin | 4.0 |
| (7) dibutylhydroxytoluene | 0.02 |
| (8) propyl p-oxybenzoate | 0.2 |
| (9) carboxymethylcellulose | 0.1 |
| (10) 1,3-butylene glycol | 5.0 |
| (11) perfume | 0.2 |
| (12) purified water | balance |

Preparation

First, ingredients (1) to (8) were mixed and heated to 75° C., and then, while stirring the mixture, previously mixed ingredients (9), (10) and (12) previously heated to 75° C. were gradually added to the mixture to carry out the emulsification. After cooling the mixture, an ingredient (11) was added to the mixture to obtain a milk lotion.

The obtained milk lotion was excellent in emulsification stability for a long period of time, and its usage feeling was also excellent.

EXAMPLE 29

Hair Cream (Water-in-Oil Type)

| (Compositions) | (weight %) |
|---|---|
| (1) siloxane derivative (A) | 2.0 |
| (2) sodium salicylate | 0.7 |
| (3) liquid paraffin | 5.5 |
| (4) dimethylpolysiloxane | 4.5 |
| (5) glycerol | 10.0 |
| (6) perfume | 0.1 |
| (7) purified water | balance |

Preparation

First, ingredients (1) to (4) were mixed and heated to 75° C., and then, while stirring the mixture, previously mixed ingredients (5) and (7) previously heated to 75° C. were gradually added to the mixture to carry out the emulsification. After cooling the mixture, an ingredient (6) was added to the mixture to obtain a hair cream.

The obtained hair cream exhibited excellent emulsification stability.

EXAMPLE 30

Foundation Cream (Water-in-Oil Type)

| (Compositions) | (weight %) |
|---|---|
| (1) siloxane derivative (N) | 2.0 |
| (2) potassium sorbitanate | 0.05 |
| (3) magnesium sulfate | 1.0 |
| (4) polyoxyethylene(7)sorbitoltetraoleate | 3.5 |
| (5) liquid paraffin | 8.5 |
| (6) volatile silicone | 1.0 |
| (7) talc | 6.0 |
| (8) Kaolin | 8.0 |
| (9) titanium oxide | 1.0 |
| (10) iron oxide | 0.5 |
| (11) glycerol | 8.0 |
| (12) perfume | 0.05 |
| (13) purified water | balance |

Preparation

First, ingredients (1) to (6) were mixed and heated to 75° C., and then, while stirring the mixture, previously mixed ingredients (11) and (13) previously heated to 75° C. were gradually added to the mixture to carry out the emulsification. Then, ingredients (7) to (10) were added to the mixture, and the mixture was uniformly kneaded. After cooling the mixture, an ingredient (13) was added to the mixture to obtain a foundation cream.

The obtained foundation cream was excellent in emulsification stability for a long period of time, and its usage feeling was also excellent.

Although the present invention has been described in its preferred embodiments, it is readily understood that the present invention is not restricted to the preferred embodiments and that various changes and modifications thereof can be made by those skilled in the art without departing from the spirit and scope of the present invention.

What is claimed is:

1. A siloxane derivative represented by general formula (1)

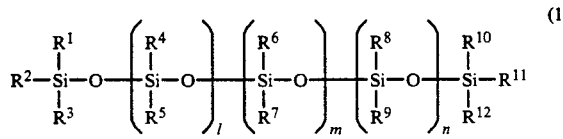

wherein at least one of $R^1$ to $R^{12}$ is a group represented by general formula (2)

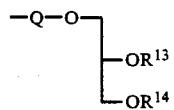

wherein Q is a divalent hydrocarbon group having 3 to 20 carbon atoms, $R^{13}$ and $R^{14}$ are hydrogen atom or a hydrocarbon group having 1 to 5 carbon atoms, and at least one of $R^{13}$ and $R^{14}$ is hydrogen atom; the remainings of $R^1$ to $R^{12}$ are straight-chain, branched-chain or cyclic hydrocarbon groups having 1 to 30 carbon atoms or groups represented by general formula (3)

wherein X is a divalent hydrocarbon group having an ether bonding and/or ester bonding and $R^{15}$ is a straight-chain, branched-chain or cyclic hydrocarbon group having 1 to 30 carbon atoms; l, m and n are numbers of 0 to 2000, and at least one of $R^1$ to $R^3$ and $R^{10}$ to $R^{12}$ is a group represented by general formula (2) when $l+m+n=0$ except that one of $R^1$ to $R^{12}$ is a group represented by general formula (2) wherein Q is trimethylene and $R^{13}$ and $R^{14}$ are both hydrogen atoms; and the remainings of $R^1$ to $R^{12}$ are all methyl groups.

2. The siloxane derivative of claim 1, wherein Q is an alkylene group having 3 to 20 carbon atoms and $R^{13}$ and $R^{14}$ are hydrogen atoms, and wherein $R^1$ to $R^{12}$ are alkyl groups having 1 to 30 carbon atoms.

3. The siloxane derivative of claim 1, wherein $l+m+n$ is 0 to 2000 and Q is an alkylene group having 3 to 20 carbon atoms.

4. The siloxane derivative of claim 1, wherein the siloxane derivative is represented by general formula (1A)

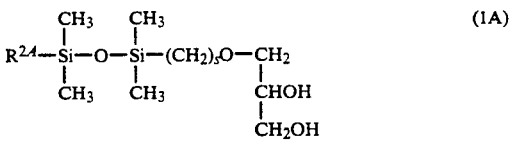

wherein $R^{24}$ represents an alkyl group having 2 to 30 carbon atoms and s is a number of 3 to 20.

5. The siloxane derivative of claim 1, wherein the siloxane derivative is represented by general formula (1B)

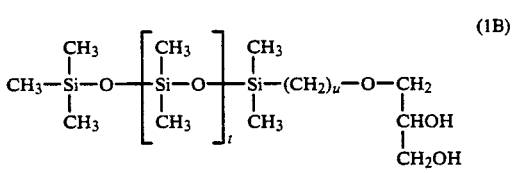

wherein t is a number of 0 to 2000 and u is a number of 3 to 20.

6. The siloxane derivative of claim 1, wherein the siloxane derivative is represented by general formula (1C)

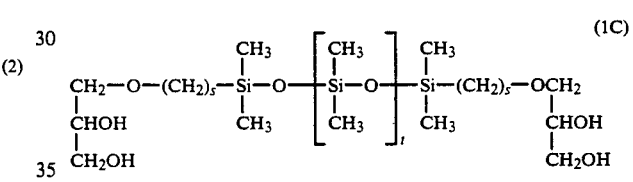

wherein t is a number of 0 to 2000 and s is a number of 3 to 20.

7. The siloxane derivative of claim 1, wherein the siloxane derivative is represented by general formula (1D)

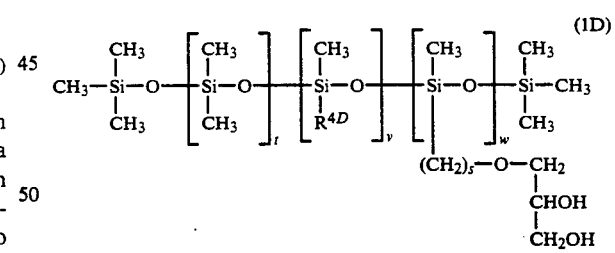

wherein $R^{4D}$ represents an alkyl group having 2 to 30 carbon atoms, t and v are numbers of 0 to 1000, w is a number of 1 to 1000, and s is a number of 3 to 20.

8. A method for producing a siloxane derivative represented by general formula (1a)

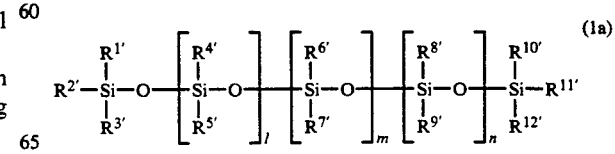

wherein at least one of $R^{1'}$ to $R^{12'}$ represents a group represented by general formula (2)

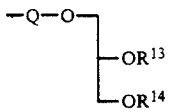

wherein Q is a divalent hydrocarbon group having 3 to 20 carbon atoms, $R^{13}$ and $R^{14}$ are hydrogen atom or a hydrocarbon group having 1 to 5 carbon atoms, and at least one of $R^{13}$ and $R^{14}$ is hydrogen atom; the remainings of $R^{1'}$ to $R^{12'}$ are straight-chain, branched-chain or cyclic hydrocarbon groups having 1 to 30 carbon atoms, and at least one of $R^{1'}$ to $R^{3'}$ and $R^{10'}$ to $R^{12'}$ represents a group represented by general formula (2) when $1+m+n=0$ except that one of $R^{1'}$ to $R^{12'}$ represents a group represented by general formula (2) wherein Q represents trimethylene and $R^{13}$ and $R^{14}$ represent both hydrogen atoms, and the remainings of $R^{1}$ to $R^{12}$ represent all methyl groups, comprising reacting a compound represented by general formula (4)

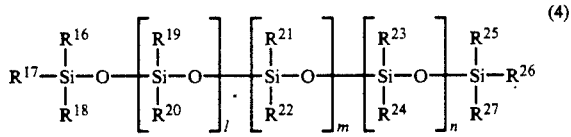

wherein at least one of $R^{16}$ to $R^{27}$ represents hydrogen atom, the remainings of $R^{16}$ to $R^{27}$ represent a straight-chain, branched-chain or cyclic hydrocarbon group having 1 to 30 carbon atoms, l, m and n are numbers of 0 to 2000, and at least one of $R^{16}$ to $R^{18}$ and $R^{25}$ to $R^{27}$ represents hydrogen atom when $1+m+n=0$, with a compound represented by general formula (2')

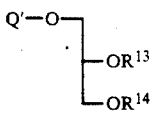

In formula (2'), Q' represents a hydrocarbon group having 3 to 20 carbon atoms and one double bond, and $R^{13}$ and $R^{14}$ are the same as described above.

9. A method for producing a siloxane derivative represented by general formula (1b)

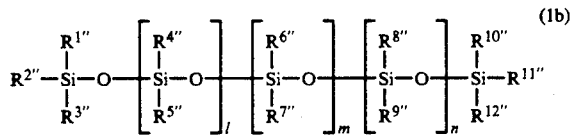

wherein at least one of $R^{1'''}$ to $R^{12'''}$ represents a group represented by general formula (2)

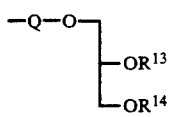

wherein Q is a divalent hydrocarbon group having 3 to 20 carbon atoms, $R^{13}$ and $R^{14}$ are hydrogen atom or a hydrocarbon group having 1 to 5 carbon atoms, and at least one of $R^{13}$ and $R^{14}$ is hydrogen atom; at least one of the remainings of $R^{1'''}$ to $R^{12'''}$ represents a group represented by general formula (3)

$$-X-R^{15} \quad (3)$$

wherein X is a divalent hydrocarbon group having an ether bonding and/or ester bonding and $R^{15}$ is a straight-chain, branched-chain or cyclic hydrocarbon group having 1 to 30 carbon atoms; and the remainings of $R^{1'''}$ to $R^{12'''}$ are straight-chain, branched-chain or cyclic hydrocarbon groups having 1 to 30 carbon atoms, and, when $1+m+n=0$, at least one of $R^{1'''}$ to $R^{3'''}$ and $R^{10'''}$ to $R^{12'''}$ represents a group represented by general formula (2) and at least one of the remainings of $R^{1'''}$ to $R^{3'''}$ and $R^{10'''}$ to $R^{12'''}$ represents a group represented by general formula (3), comprising reacting a compound represented by general formula (4')

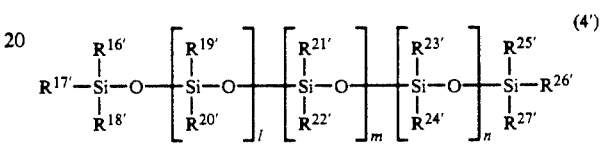

wherein at least two of $R^{16'}$ to $R^{27'}$ represent hydrogen atoms, the remainings of $R^{16'}$ to $R^{27'}$ represent a straight-chain, branched-chain or cyclic hydrocarbon group having 1 to 30 carbon atoms, l, m and n are the same as described above, and at least two of $R^{16'}$ to $R^{16'}$ and $R^{25'}$ to $R^{27'}$ represent hydrogen atoms when $1+m+n=0$, with compounds represented by general formulas (2') and (3')

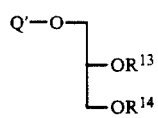

wherein Q' represents a hydrocarbon group having 3 to 20 carbon atoms and one double bond, and $R^{13}$ and $R^{14}$ are the same as described above, and $$X'-R^{15} \quad (3')$$

wherein X' is a hydrocarbon group having at least one double bond and an ether bonding and/or ester bonding and $R^{15}$ is the same as described above.

10. A use as an emulsifier of a siloxane derivative specified in claim 1.

11. A cosmetic preparation including a siloxane derivative represented by general formula (1) specified in claim 1.

12. A emulsifying dermatotherapeutic external agent comprising:
 (A) 5 to 70 weight % of oil phase component;
 (B) 20 to 94.9 weight % of water phase component; and
 (C) 0.1 to 30 weight % of emulsifier including a siloxane derivative represented by general formula (1)

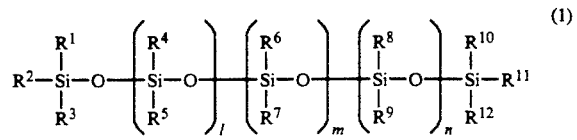

wherein at least one of $R^1$ to $R^{12}$ is a group represented by general formula (2)

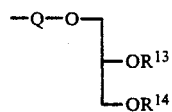

wherein Q is a divalent hydrocarbon group having 3 to 20 carbon atoms, $R^{13}$ and $R^{14}$ are hydrogen atom or a hydrocarbon group having 1 to 5 carbon atoms, and at least one of $R^{13}$ and $R^{14}$ is hydrogen atom; the remainings of $R^1$ to $R^{12}$ are straight-chain, branched-chain or cyclic hydrocarbon groups having 1 to 30 carbon atoms or groups represented by general formula (3)

$$-X-R^{15} \qquad (3)$$

wherein X is a divalent hydrocarbon group having an ether bonding and/or ester bonding and $R^{15}$ is a straight-chain, branched-chain or cyclic hydrocarbon group having 1 to 30 carbon atoms; l, m and n are numbers of 0 to 200, and at least one of $R^1$ to $R^3$ and $R^{10}$ to $R^{12}$ is a group represented by general formula (2) when $l+m+n=0$ except that one of $R^1$ to $R^{12}$ is a group represented by general formula (2) wherein Q is trimethylene and $R^{13}$ and $R^{14}$ are both hydrogen atoms; and the remainings of $R^1$ to $R^{12}$ are all methyl groups.

13. The emulsifying dermatotherapeutic external agent of claim 12, wherein the oil phase component (A) includes at most 50 weight % of silicone oil, and wherein in the siloxane derivative of the component (C), $l+m+n$ is 0 to 2000 and Q is an alkylene group having 3 to 20 carbon atoms.

14. The emulsifying dermatotherapeutic external agent of claim 12, wherein the oil phase component (A) includes 50 weight % of silicone oil, and wherein the siloxane derivative in component (C) is represented by either one of the following formulae (1A) to (1D):

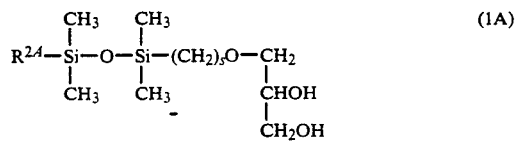

wherein $R^{2A}$ represents an alkyl group having 2 to 30 carbon atoms and s is a number of 3 to 20,

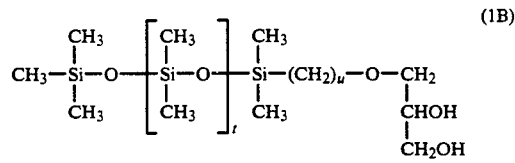

wherein t is a number of 0 to 2000 and u is a number of 3 to 20,

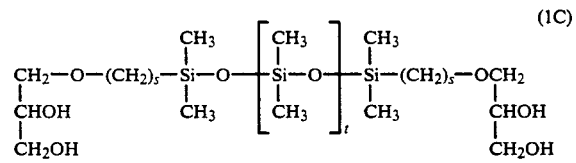

wherein, t is a number of 0 to 2000 and s is a number of 3 to 20,

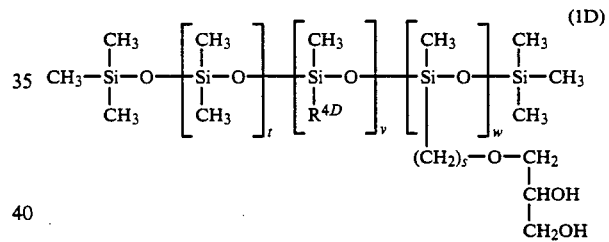

wherein $R^{4D}$ represents an alkyl group having 2 to 30 carbon atoms, t and v are numbers of 0 to 1000, w is a number of 1 to 1000, and s is a number of 3 to 20.

* * * * *